(12) United States Patent
Maurer et al.

(10) Patent No.: US 7,345,080 B2
(45) Date of Patent: Mar. 18, 2008

(54) SUBSTITUTED 4-PYRAZOLYL PYRAZONLINES USED FOR PEST CONTROL

(75) Inventors: Fritz Maurer, Lauffen (DE); Rainer Fuchs, Wuppertal (DE); Christoph Erdelen, deceased, late of Leichlingen (DE); by Angelika Lubos-Erdelen, legal representative, Leichlingen (DE); Jörg Konze, Köln (DE); Andreas Turberg, Haan (DE)

(73) Assignee: Bayer CropScience AG, Monheim (DE)

( * ) Notice: Subject to any disclaimer, the term of this patent is extended or adjusted under 35 U.S.C. 154(b) by 563 days.

(21) Appl. No.: 10/504,357

(22) PCT Filed: Feb. 23, 2003

(86) PCT No.: PCT/EP03/01179

§ 371 (c)(1),
(2), (4) Date: Feb. 11, 2005

(87) PCT Pub. No.: WO03/070724

PCT Pub. Date: Aug. 28, 2003

(65) Prior Publication Data

US 2005/0159603 A1    Jul. 21, 2005

(30) Foreign Application Priority Data

Feb. 19, 2002 (DE) .................. 102 06 791

(51) Int. Cl.
A01N 43/56 (2006.01)
C07D 403/04 (2006.01)

(52) U.S. Cl. ................. 514/406; 548/365.4
(58) Field of Classification Search ........ 514/406; 548/365.4
See application file for complete search history.

(56) References Cited

U.S. PATENT DOCUMENTS 5,380,868 A    1/1995   Gallenkamp et al. .... 548/365.4
5,410,066 A    4/1995   Gallenkamp et al. .... 548/375.1

FOREIGN PATENT DOCUMENTS

| DE | 44 16 112 | 11/1995 |
|---|---|---|
| DE | 10135551 A | * 1/2003 |
| EP | 0 438 690 | 7/1991 |
| EP | 0 679 664 | 11/1995 |
| WO | 94/29268 | 12/1994 |

OTHER PUBLICATIONS

Chem. Ind., 37, (month unavailable) 1985, pp. 730-732, Harry R. Ungerer, "Schiffsfarben—eine Spezialität der seenahen Lackindustrie".

* cited by examiner

*Primary Examiner*—Kamal A. Saeed
(74) *Attorney, Agent, or Firm*—Richard E. L. Henderson

(57) ABSTRACT

This invention relates to novel substituted 4-pyrazolylpyrazolines of formula (I)

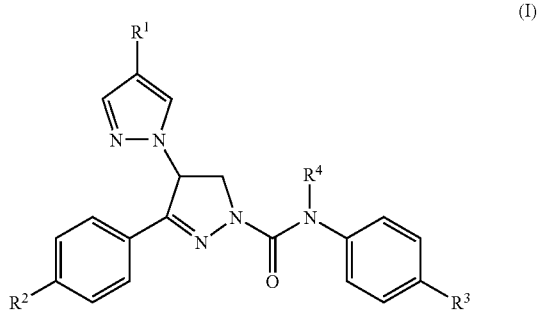

in which $R^1$, $R^2$, $R^3$ and $R^4$ are as defined in the disclosure, to a plurality of processes for preparing these substances and their use for controlling pests, and to novel intermediates and processes for their preparation.

18 Claims, No Drawings

SUBSTITUTED 4-PYRAZOLYL PYRAZONLINES USED FOR PEST CONTROL

The present patent application has been filed under 35 U.S.C. 371 as a national stage application of PCT/EP03/01179, filed Feb. 6, 2003, which was published in German as International Patent Publication WO 03/070724 on Aug. 28, 2003, which is entitled to the right of priority of German Patent Application 1002 06 791.0, filed Feb. 19, 2002.

It is known that certain substituted 4-pyrazolylpyrazolines have insecticidal and acaricidal properties (cf., for example, DE-A 44 16 112, EP-A 0 679 644 or EP-A 0 438 690). However, the activity of these compounds is, in particular at low active compound concentrations and application rates, not always entirely satisfactory.

This invention provides novel substituted 4-pyrazolylpyrazolines of the formula (I)

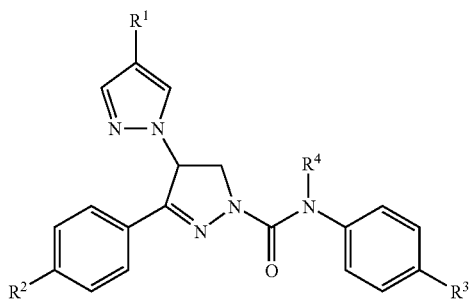

in which $R^1$ represents optionally substituted hetaryl, $R^2$ represents halogen, haloalkyl, alkoxy, haloalkoxy, alkylthio, haloalkylthio, alkylsulphonyl, haloalkylsulphinyl, haloalkylsulphonyl or cyano, $R^3$ represents halogen, haloalkyl, alkoxy, haloalkoxy, alkylthio, haloalkylthio, haloalkylsulphinyl, haloalkylsulphonyl or cyano and $R^4$ represents hydrogen, cyanomethyl or alkoxycarbonyl.

Depending on the nature and number of substituents, the compounds of the formula (I) can, if appropriate, be present as geometrical and/or optical isomers, regioisomers and/or configurational isomers or isomer mixtures thereof of varying compositions. What is claimed by the invention are both the pure isomers and the isomer mixtures.

Furthermore, it has been found that the substituted pyrazolines of the formula (I) are obtained when a) pyrazolines of the formula (II)

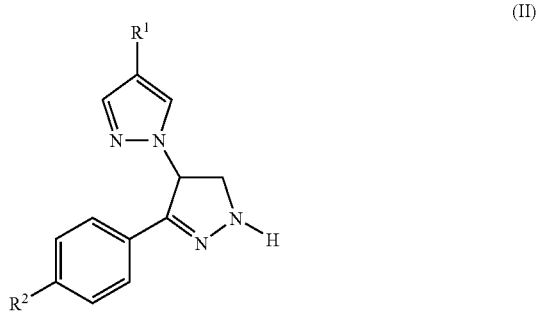

in which $R^1$ and $R^2$ are as defined above are reacted with isocyanates of the formula (III)

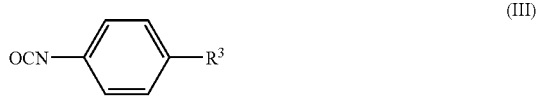

in which $R^3$ is as defined above, if appropriate in the presence of a diluent and if appropriate in the presence of a catalyst;

and b) the resulting pyrazoline derivatives of the formula (Ia) according to the invention

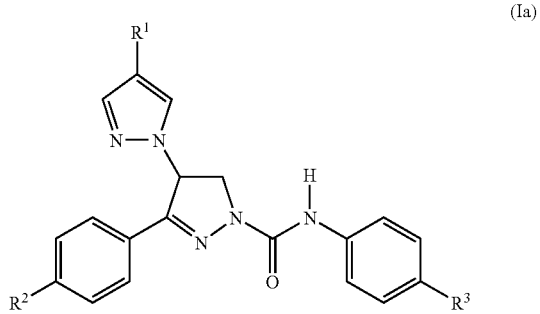

in which $R^1$, $R^2$ and $R^3$ are as defined above are, if appropriate, reacted with halides of the formula (IV)

$$Hal^1 - R^4 \qquad (IV)$$

in which $R^4$ is as defined above and $Hal^1$ represents halogen, if appropriate in the presence of a diluent and if appropriate in the presence of a base;

or c) anilines of the formula (V)

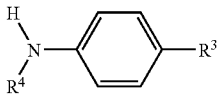

(V)

in which
R³ and R⁴ are as defined above
are initially reacted with phosgene in the presence of a diluent and, if appropriate, in the presence of a base, and the resulting carbamoyl chlorides of the formula (VI)

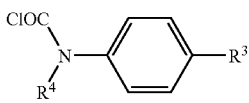

(VI)

in which
R³ and R⁴ are as defined above
are, directly or after intermediate isolation, reacted with pyrazolines of the formula (II)

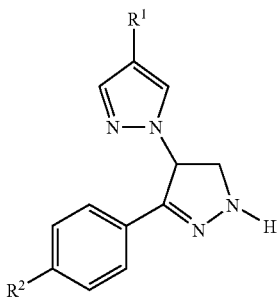

(II)

in which
R¹ and R² are as defined above,
in the presence of a diluent and, if appropriate, in the presence of a base.

Finally, it has been found that the novel substituted 4-pyrazolylpyrazolines of the formula (I) have strongly pronounced biological properties and are suitable especially for controlling animal pests, in particular insects, arachnids and nematodes, encounted in agriculture, in forests, in the protection of stored products and materials and in the hygiene sector.

The formula (I) provides a general definition of the 4-pyrazolylpyrazolines according to the invention.

Preferred substituents or ranges of the radicals listed in the formulae mentioned above and below are illustrated below:

$R^1$ preferably represents oxadiazolyl or thiadiazolyl, each of which is optionally monosubstituted, exemplary substituents which may be mentioned being:
optionally substituted alkyl, optionally substituted alkoxy, optionally substituted alkylthio, optionally substituted aryl or optionally substituted arylalkyl; or
represents optionally monosubstituted tetrazolyl, exemplary substituents which may be mentioned being: optionally substituted alkyl, optionally substituted alkylthio or alkylsulphonyl, in each case optionally substituted aryl or arylalkyl or optionally substituted cycloalkyl.

$R^2$ preferably represents fluorine, chlorine, bromine, iodine; $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphonyl, $C_1$-$C_4$-haloalkylsulphinyl, $C_1$-$C_4$-haloalkylsulphonyl or cyano.

$R^3$ Preferably represents fluorine, chlorine, bromine, iodine; $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-haloalkylsulphinyl, $C_1$-$C_4$-haloalkylsulphonyl or cyano.

$R^4$ preferably represents hydrogen, cyanomethyl or $C_1$-$C_4$-alkoxycarbonyl.

$R^1$ particularly preferably represents oxadiazolyl or thiadiazolyl, each of which is optionally monosubstituted, exemplary substituents which may be mentioned being: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, and also phenyl or benzyl, each of which is optionally mono- to trisubstituted by identical or different substituents from the group consisting of halogen, $C_1$-$C_4$-haloalkyl and $C_1$-$C_4$-haloalkoxy; or represents optionally monosubstituted tetrazolyl, substituents which may be mentioned being: $C_1$-$C_4$-alkyl, $C_1$-$C_4$-haloalkyl, $C_1$-$C_4$-alkylthio, $C_1$-$C_4$-alkylsulphonyl, and also phenyl or benzyl, each of which is optionally mono- to trisubstituted by identical or different substituents from the group consisting of halogen, $C_1$-$C_4$-haloalkyl and $C_1$-$C_4$-haloalkoxy, furthermore cyclopentyl or cyclohexyl, each of which is optionally mono- to trisubstituted by identical or different $C_1$-$C_4$-alkyl.

$R^2$ particularly preferably represents fluorine, chlorine, bromine, iodine, cyano, $C_1$-$C_2$-alkylthio, $C_1$-$C_2$-alkylsulphonyl, and also represents $C_1$-$C_2$-haloalkyl, $C_1$-$C_2$-haloalkoxy, $C_1$-$C_2$-haloalkylthio or $C_1$-$C_2$-haloalkylsulphonyl having in each case 1 to 5 identical or different halogen atoms from the group consisting of fluorine, chlorine and bromine.

$R^3$ particularly preferably represents chlorine, bromine, iodine, cyano; and also represents $C_1$-$C_2$-haloalkyl, $C_1$-$C_2$-haloalkoxy, $C_1$-$C_2$-haloalkylthio, $C_1$-$C_2$-haloalkylsulphinyl or $C_1$-$C_2$-haloalkylsulphonyl having in each case 1 to 5 identical or different halogen atoms from the group consisting of fluorine, chlorine and bromine.

$R^4$ particularly preferably represents hydrogen, cyanomethyl or $C_1$-$C_4$-alkoxycarbonyl.

$R^1$ very particular preferably represents an oxadiazolyl group from the group consisting of:

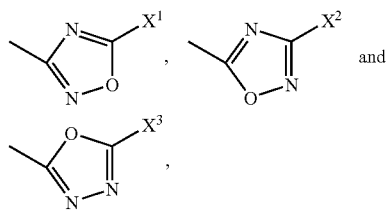

where
$X^1$, $X^2$ and $X^3$ independently of one another represent hydrogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio and also represent phenyl or benzyl, each of which is optionally mono- to trisubstituted by identical or different substituents from the group consisting of halogen, $C_1$-$C_2$-haloalkyl and $C_1$-$C_2$-haloalkoxy having in each case 1 to 3 identical or different halogen atoms from the group consisting of fluorine, chlorine and bromine; or represents a tetrazolyl group from the group consisting of:

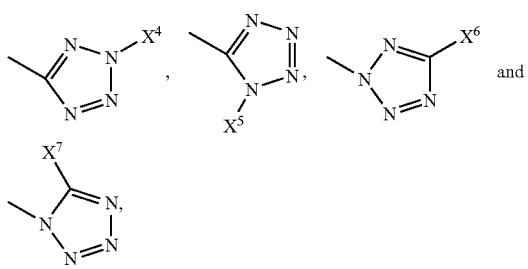

where $X^4$, $X^5$, $X^6$ and $X^7$ independently of one another represent hydrogen, $C_1$-$C_4$-alkyl, $C_1$-$C_2$-haloalkyl having 1 to 3 identical or different halogen atoms from the group consisting of fluorine, chlorine and bromine; $C_1$-$C_4$-alkylthio, $C_1$-$C_4$-alkylsulphonyl, represent phenyl or benzyl, each of which is optionally mono- to trisubstituted by identical or different substituents from the group consisting of halogen, $C_1$-$C_2$-haloalkyl and $C_1$-$C_2$-haloalkoxy having in each case 1 to 3 identical or different halogen atoms from the group consisting of fluorine, chlorine and bromine; and also represent cyclopentyl or cyclohexyl, each of which is optionally mono- to trisubstituted by identical or different $C_1$-$C_4$-alkyl.

$R^2$ very particular preferably represents fluorine, chlorine, bromine, iodine, methylthio, trifluoromethyl, trifluoromethoxy or trifluoromethylthio.

$R^3$ very particular preferably represents chlorine, bromine, iodine, cyano; trifluoromethyl, trifluoromethoxy, trifluoromethylthio, trifluoromethylsulphinyl or trifluoromethylsulphonyl.

$R^4$ very particular preferably represents hydrogen, cyanomethyl, methoxycarbonyl, ethoxycarbonyl, n- or i-propoxycarbonyl, n-, i-, s- or t-butoxycarbonyl.

$R^1$ especially preferably represents an oxadiazolyl group from the group consisting of:

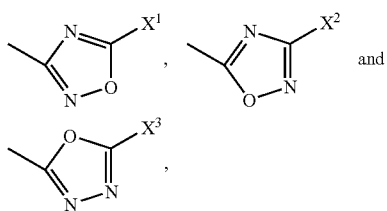

where $X^1$, $X^2$ and $X^3$ independently of one another represent hydrogen, methyl, ethyl, n- or i-propyl, n-, i-, s- or t-butyl, trifluoromethyl, trifluoromethoxy or trifluoromethylthio and also represent phenyl or benzyl, each of which is optionally mono- or disubstituted by identical or different substituents from the group consisting of fluorine, chlorine, bromine, trifluoromethyl and trifluoromethoxy;

represents a tetrazolyl group from the group consisting of:

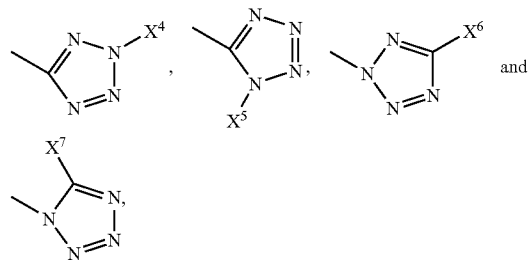

where $X^4$, $X^5$, $X^6$ and $X^7$ independently of one another represent hydrogen, methyl, ethyl, n- or i-propyl, n-, i-, s- or t-butyl; fluoromethyl, difluoromethyl, trifluoromethyl, 1,1-difluoroethyl, 2,2,2-trifluoroethyl, methylthio, ethylthio, methylsulphonyl, ethylsulphonyl; represent phenyl or benzyl, each of which is optionally mono- or disubstituted by identical or different substituents from the group consisting of fluorine, chlorine, bromine, trifluoromethyl and trifluoromethoxy; and also represent cyclohexyl which is optionally mono- or disubstituted by methyl.

$R^2$ especially preferably represents fluorine, chlorine, bromine, iodine or trifluoromethylthio.

$R^3$ especially preferably represents chlorine, bromine, iodine, cyano; trifluoromethyl, trifluoromethoxy, trifluoromethylthio, trifluoromethylsulphinyl or trifluoromethylsulphonyl.

$R^4$ especially preferably represents hydrogen or cyanomethyl.

Preference is furthermore given to compounds of the formula (I) in which $R^2$ represents halogen, preferably fluorine, chlorine, bromine, iodine, particularly preferably fluorine or chlorine, very particularly preferably chlorine.

Preference is furthermore given to compounds of the formula (I) in which $R^3$ represents fluorine, chlorine, bromine, iodine, cyano; and also represents $C_1$-$C_2$-haloalkyl, $C_1$-$C_2$-haloalkoxy, $C_1$-$C_2$-haloalkylsulphinyl or $C_1$-$C_2$-haloalkylsulphonyl having in each case 1 to 5 identical or different halogen atoms from the group consisting of fluorine, chlorine and bromine; particularly preferably represents chlorine, trifluoromethyl, trifluoromethoxy or trifluoromethylthio.

Preference is furthermore given to compounds of the formula (I) in which $R^4$ represents hydrogen or cyanomethyl.

Preference is furthermore given to compounds of the formula (I) in which $R^2$ represents chlorine and $R^4$ represents hydrogen or cyanomethyl.

Preference is furthermore given to compounds of the formula (I) in which $R^1$ represents oxadiazolyl or thiadiazolyl, each of which is optionally monosubstituted, exemplary substituents which may be mentioned being: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, and also phenyl or benzyl, each of which is optionally mono- to trisubstituted by identical or different substituents from the group consisting of halogen, $C_1$-$C_4$-haloalkyl and $C_1$-$C_4$-haloalkoxy;

preferably represents an oxadiazolyl group from the group consisting of:

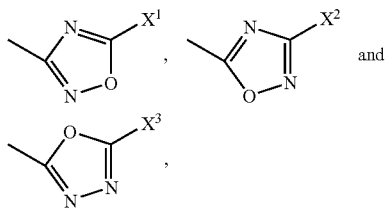

where
X$^1$, X$^2$ and X$^3$ independently of one another represent hydrogen, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio, C$_1$-C$_4$-haloalkylthio and also represent phenyl or benzyl, each of which is optionally mono- to trisubstituted by identical or different substituents from the group consisting of halogen, C$_1$-C$_2$-haloalkyl and C$_1$-C$_2$-haloalkoxy having in each case 1 to 3 identical or different halogen atoms from the group consisting of fluorine, chlorine and bromine;

particularly preferably represents an oxadiazolyl group from the group consisting of:

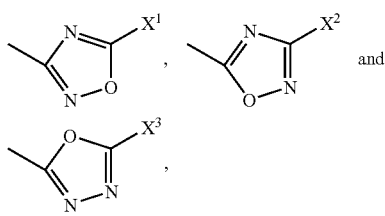

where
X$^1$, X$^2$ and X$^{3'}$ independently of one another represent hydrogen, methyl, ethyl, n- or i-propyl, n-, i-, s- or t-butyl, trifluoromethyl, trifluoromethoxy or trifluoromethylthio and also represent phenyl or benzyl, each of which is optionally mono- or disubstituted by identical or different substituents from the group consisting of fluorine, chlorine, bromine, trifluoromethyl and trifluoromethoxy;

very particularly preferably represent the oxadiazolyl groups

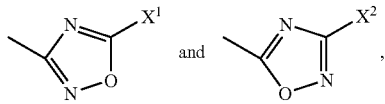

where
X$^1$ and X$^2$ independently of one another represent methyl, ethyl, t-butyl or trifluoromethyl.

Preference is furthermore given to compounds of the formula (I) in which R$^1$ represents optionally monosubstituted tetrazolyl, substituents that may be mentioned being: C$_1$-C$_4$-alkyl, C$_1$-C$_4$-haloalkyl, C$_1$-C$_4$-alkylthio, C$_1$-C$_4$-alkylsulphonyl, and also phenyl or benzyl, each of which is optionally mono- to trisubstituted by identical or different substituents from the group consisting of halogen, C$_1$-C$_4$-haloalkyl and C$_1$-C$_4$-haloalkoxy, furthermore cyclopentyl or cyclohexyl, each of which is optionally mono- to trisubstituted by identical or different C$_1$-C$_4$-alkyl;

preferably represents a tetrazolyl group from the group consisting of:

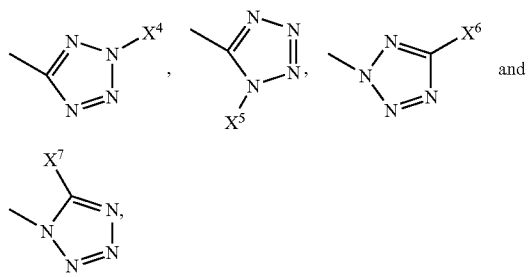

where
X$^4$, X$^5$, X$^6$ and X$^7$ independently of one another represent hydrogen, C$_1$-C$_4$-alkyl, C$_1$-C$_2$-haloalkyl having 1 to 3 identical or different halogen atoms from the group consisting of fluorine, chlorine and bromine; C$_1$-C$_4$-alkylthio, C$_1$-C$_4$-alkylsulphonyl, represent phenyl or benzyl, each of which is optionally mono- to trisubstituted by identical or different substituents from the group consisting of halogen, C$_1$-C$_2$-haloalkyl and C$_1$-C$_2$-haloalkoxy having in each case 1 to 3 identical or different halogen atoms from the group consisting of fluorine, chlorine and bromine; and also represents cyclopentyl or cyclohexyl, each of which is optionally mono- to trisubstituted by identical or different C$_1$-C$_4$-alkyl;

particularly preferably represents a tetrazolyl group from the group consisting of:

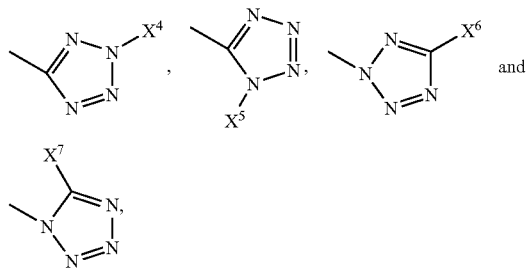

where
X$^4$, X$^5$, X$^6$ and X$^7$ independently of one another represent hydrogen, methyl, ethyl, n- or i-propyl, n-, i-, s- or t-butyl; fluoromethyl, difluoromethyl, trifluoromethyl, 1,1-difluoroethyl, 2,2,2-trifluoroethyl, methylthio, ethylthio, methylsulphonyl, ethylsulphonyl; represent phenyl or benzyl, each of which is optionally mono- or disubstituted by identical or different substituents from the group consisting of fluorine, chlorine, bromine, trifluoromethyl and trifluoromethoxy; and also represent cyclohexyl which is optionally mono- or disubstituted by methyl;

very particularly preferably represents the tetrazolyl groups

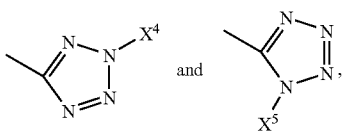

where
X⁴ and X⁵ independently of one another represent methyl, ethyl, t-butyl or trifluoromethyl.

The general or preferred radical definition or illustrations listed above can also be combined with one another as desired, i.e. including combinations between the respective ranges and preferred ranges. The definitions apply both to the end products and, correspondingly, to precursors and intermediates. Moreover, individual definitions may not apply.

In the radical definitions given above and below, hydrocarbon radicals, such as alkyl, are in each case straight-chain or branched as far as this is possible—including in combination with heteroatoms, such as alkoxy.

Halogen-substituted radicals, for example haloalkyl, are mono- or polyhalogenated up to the maximum possible number of substituents. In the case of polyhalogenation, the halogen atoms can be identical or different. Here, halogen represents fluorine, chlorine, bromine or iodine, in particular fluorine, chlorine or bromine.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Special preference according to the invention is given to the compounds of the formula (I) which contain a combination of the meanings listed above as being especially preferred.

Using, for example, 3-(4-chlorophenyl)-4-[4-(2-tert-butyltetrazol-5-yl)-pyrazol-1-yl]-4,5-dihydro-1H-pyrazole and 4-trifluoromethoxyphenyl isocyanate as starting materials, the course of the reaction of the process (a) according to the invention can be represented by the equation below:

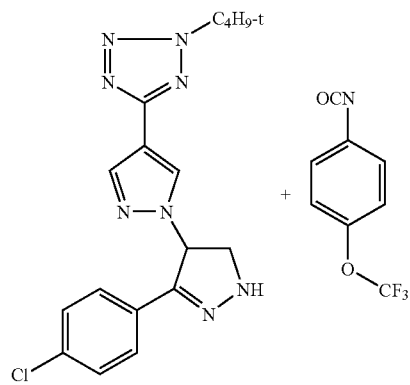

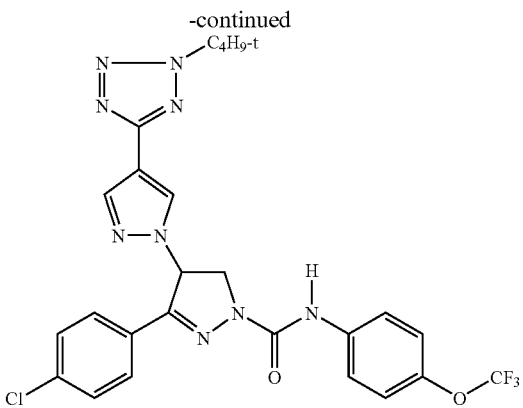

Using, for example, N-(4-trifluoromethoxy)-3-(4-chlorophenyl)-4-[4-(2-tert-butyltetrazol-5-yl)-pyrazol-1-yl]-4,5-dihydro-1-pyrazolcarboxanilide and bromoacetonitrile as starting materials, the course of the reaction of the process (b) according to the invention can be represented by the following equation:

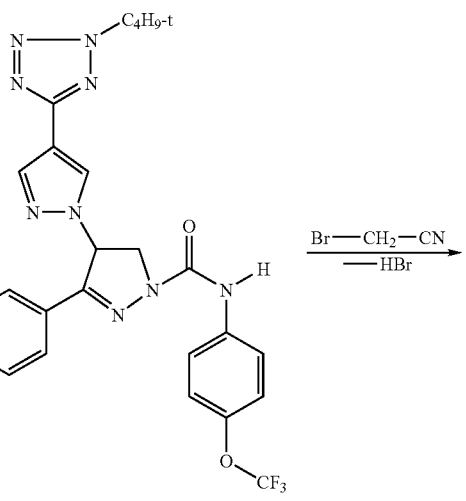

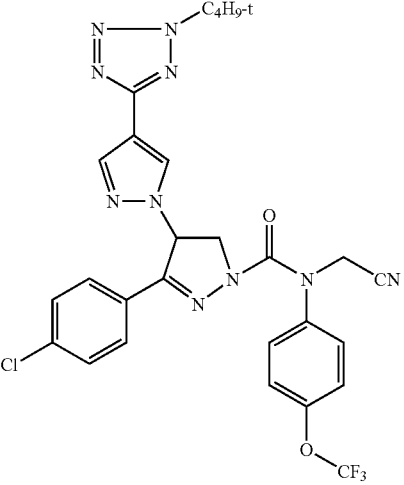

Using, for example, N-cyanomethyl-4-trifluoromethoxyaniline, phosgene and 3-(4-chlorophenyl)-4-[4-(2-tert-butyltetrazol-5-yl)-pyrazol-1-yl]-4,5-dihydro-1H- pyrazole as starting materials, the course of the reaction of the process (c) according to the invention can be represented by the following equation:

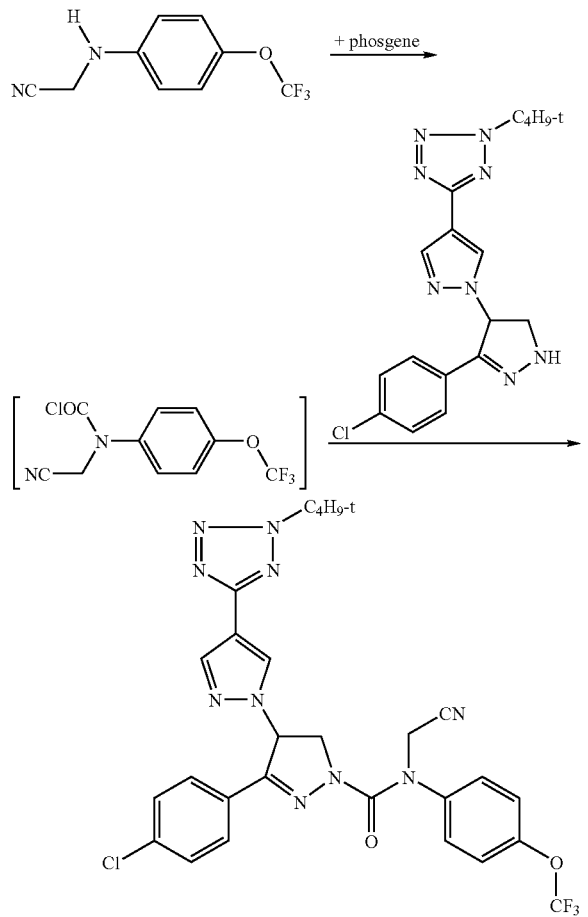

The formula (II) provides a general definition of the pyrazolines to be used as starting materials for carrying out the processes (a) and (c) according to the invention. In this formula, $R^1$ and $R^2$ preferably, particularly preferably, very particularly preferably and especially preferably have those meanings which have already been mentioned in connection with the description of the compounds of the formula (I) according to the invention as being preferred, particularly preferred, very particularly preferred and especially preferred for these radicals.

The pyrazolines of the formula (II) are novel and also form part of the subject-matter of the present application. They are obtained by reacting d) substituted acetophenones of the formula (VII)

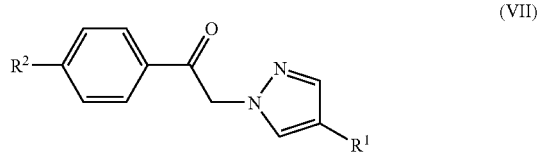

(VII)

in which
$R^1$ and $R^2$ are as defined above in a first step with bis-dialkylaminomethanes of the formula (VIII)

$(Alk)_2N—CH_2—N(Alk)_2$      (VI)

in which
Alk represents $C_1$-$C_4$-alkyl in the presence of an inert organic solvent (preferably a halogenated hydrocarbon, such as, for example, methylene chloride and ethylene chloride) at temperatures between 0° C. and 120° C. (preferably between 20° C. and 80° C.) (cf., for example, EP-A 0 546 420), and, if appropriate, isolating the resulting dialkylaminoalkyl ketones of the formula (IX)

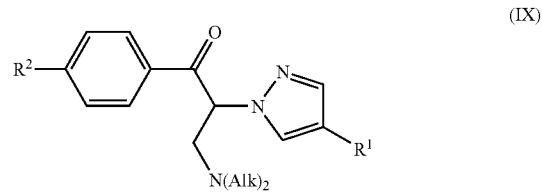

(IX)

in which
$R^1$, $R^2$ and Alk are as defined above and reacting them, in a second step, with hydrazine (hydrate) in the presence of an inert organic solvent (preferably an alcohol, such as, for example, methanol and ethanol) at temperatures between 0° C. and 80° C. (preferably between 20° C. and 50° C.) (cf. also the Preparation Examples).

The formula (VII) provides a general definition of the substituted acetophenones to be used as starting materials for carrying out the process (d) according to the invention. In this formula, $R^1$ and $R^2$ preferably, particularly preferably, very particularly preferably and especially preferably have those meanings which have already been mentioned in connection with the description of the compounds of the formula (I) according to the invention as being preferred, particularly preferred, very particularly preferred and especially preferred for these radicals.

The substituted acetophenones of the formula (VII) are novel and also form part of the subject-matter of this application. In principle, they are obtained by constructing the hetaryl radical $R^1$ in 2-(pyrazol-1-yl)-4-acetophenones which are appropriately substituted in the 4-position (for example substituted by cyano or alkoxycarbonyl).

Thus, the 2-[4-(1,2,4-oxadiazol-3-yl)-pyrazol-1-yl]acetophenones of the formula (VII a)

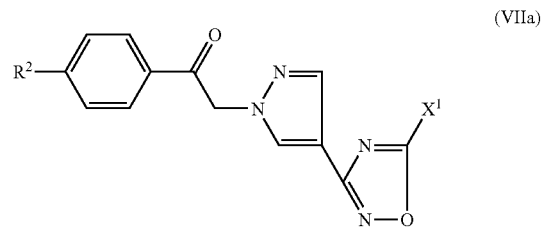

(VIIa)

in which
$R^2$ and $X^1$ are as defined above
are obtained, for example, by reacting
e) 2-(4-cyanopyrazol-1-yl)acetophenones of the formula (X)

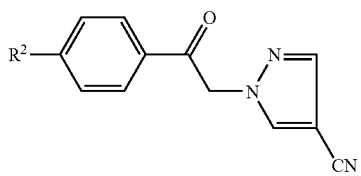

(X)

in which
R² is as defined above
with hydroxylamine hydrochloride in the presence of a diluent (preferably an aliphatic alcohol) and in the presence of a base (for example potassium carbonate) at temperatures between 20° C. and 120° C. (preferably between 50° C. and 100° C.) and reacting the resulting amidoximes of the formula (XI)

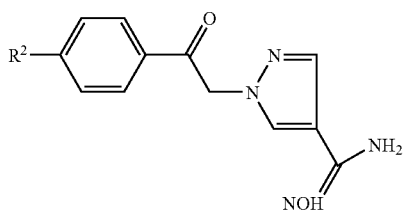

(XI)

in which
R² is as defined above
with an acetylating agent of the formula (XII)

X¹—CO-A                    (XII)

in which
A represents a leaving group, and
X¹ is as defined above,
if appropriate in the presence of an inert organic solvent (for example ethanol) and, if appropriate, in the presence of a base (for example an alkali metal alkoxide) at temperatures between 20° C. and 120° C. (preferably between 50° C. and 100° C.).

The formula (X) provides a general definition of the 2-(4-cyanopyrazol-1-yl)-acetophenones to be used as starting materials for carrying out the process (e) according to the invention. In this formula, R² preferably, particularly preferably, very particularly preferably and especially preferably has those meanings which have already been mentioned in Connection with the description of the compounds of the formula (I) according to the invention as being prefer-red, particularly prefer-red, very particularly preferred and especially preferred for this radical.

The 2-(4-cyanopyrazol-1-yl)acetophenones of the formula (X) are novel. They are obtained by reacting,
f) haloacetophenones of the formula (XII)

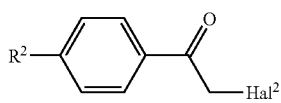

(XIII)

in which
R² is as defined above and
Hal² represents halogen with 4-cyanopyrazole in the presence of an organic or inorganic base (for example potassium carbonate) and, if appropriate, in the presence of an inert organic solvent (for example acetonitrile) at temperatures between 0° C. and 100° (preferably between 20° and 80° C.) (cf., for example, EP-A 0438 690).

The formula (XIII) provides a general definition of the haloacetophenones to be used as starting materials for carrying, out the process (f) according to the invention. In this formula, R² preferably, particularly preferably, very particularly preferably and especially preferable has those meanings which have already been mentioned in connection with the description of the compounds of the formula (I) according to the invention as being preferred, particularly preferred, very particularly preferred and especially preferred for this radical.

The haloacetophenones of the formula (X) are known compounds and/or can be obtained by known processes.

The formula (XII) provides a general definition of the acylating agents further to be used as starting materials for carrying out the process (e) according to the invention.

In this formula, X¹ preferably, particularly preferably, very particularly preferably and especially preferably has those meanings which have already been mentioned in connection with the description of the compounds of the formula (I) according to the invention as being preferred, particularly preferred, very particularly preferred and especially preferred for this radical. A preferably represents chlorine, —OC₁-C₄-alkyl or —OCOX¹.

Acylating agents of the formula (XII) are known.

Furthermore, the 2-[4-(1,2,4-oxadiazol-5-yl)pyrazol-1-yl] acetophenones of the formula (VII b)

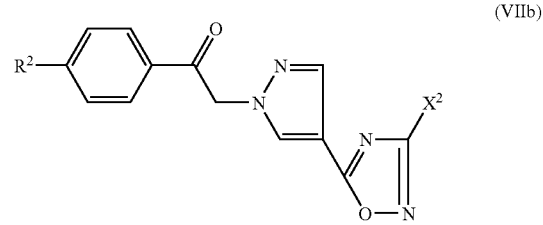

(VIIb)

in which
R² and X² are as defined above
are obtained, for example, by reacting
g) substituted 2-(pyrazol-1-yl)acetophenones of the formula (XIV)

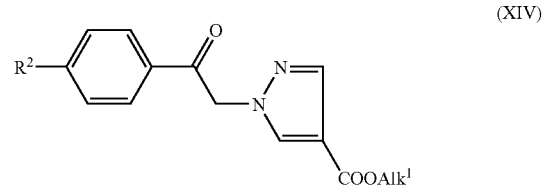

(XIV)

in which
R² is as defined above and
Alk¹ represents C₁-C₄-alkyl
with amidoximes of the formula (XV)

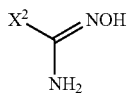

(XV)

in which

X² is as defined above, if appropriate in the presence of an inert organic solvent (such as, preferably, an aliphatic alcohol) and, if appropriate, in the presence of a base (for example an alkali metal alkoxide) at temperatures between 20° and 120° C. (preferably between 50° C. and 100° C.).

The formula (XIV) provides a general definition of the 2-(pyrazol-1-yl)acetophenones to be used as starting materials for carrying out the process (g) according to the invention. In this formula, R² preferably, particularly preferably, very particularly preferably and especially preferably has those meanings which have already been mentioned in connection with the description of the compounds of the formula (I) as being preferred, particularly preferred, very particularly preferred and especially preferred for this radical. Alk¹ preferably represents methyl, ethyl, n-, i-propyl, n-, i-, s- or t-butyl.

The 2-(pyrazol-1-yl)acetophenones of the formula (XIV) can be obtained in a generally known manner.

The formula (XV) provides a general definition of the amidoximes furthermore to be used as starting materials for carrying out the process (g) according to the invention. In this formula, X² preferably, particularly preferably, very particularly preferably and especially preferably has those meanings which have already been mentioned in connection with the description of the compounds of the formula (I) as being preferred, particularly preferred, very particularly preferred and especially preferred for this radical.

The amidoximes of the formula (XV) can be obtained in a generally known manner.

Moreover, the 2-[4-(1,3,4-oxadiazol-2-yl)pyrazol-1-yl]acetophenones of the formula (VII c)

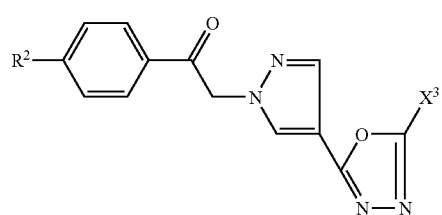

(VIIc)

in which

R² and X³ are as defined above can be obtained, for example, by heating h) substituted 2-(pyrazol-1-yl)acetophenones of the formula (XVI)

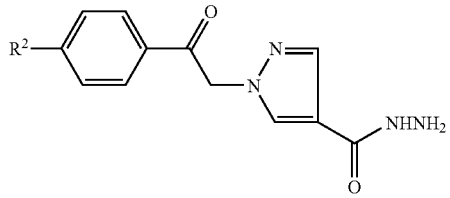

(XVI)

in which

R² is as defined above in a customary manner with appropriately (with respect to X³) substituted acetic acid derivatives, such as, preferably, alkyl esters, also in the form of the corresponding ortho esters, under reflux.

The formula (XVI) provides a general definition of the 2-(pyrazol-1-yl)acetophenones to be used as starting materials for carrying out the process (h) according to the invention. In this formula, R² preferably, particularly preferably, very particularly preferably and especially preferably has those meanings which have already been mentioned in connection with the description of the compounds of the formula (I) according to the invention as being preferred, particularly preferred, very particularly preferred and especially preferred for this radical.

The 2-(pyrazol-1-yl)acetophenones of the formula (XVI) can be obtained in a generally known manner.

Furthermore, the 2-[4-(tetrazol-5-yl)-pyrazol-1-yl]acetophenones of the formulae (VII d) and (VII e)

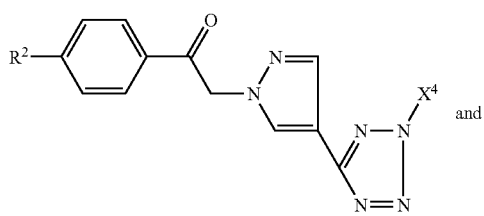

(VIId)

and

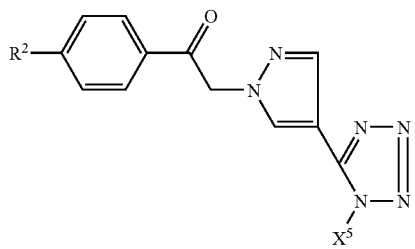

(VIIe)

in which

R², X⁴ and X⁵ are as defined above can be obtained, for example, by reacting i) 2-(4-cyanopyrazol-1-yl)acetophenones of the formula (X)

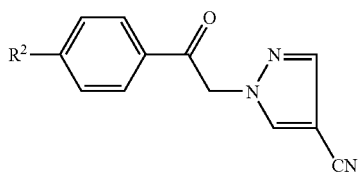

(X)

in which
R² is as defined above
with sodium azide and, for example, triethylamine hydrochloride in the presence of an inert organic solvent (for example acetonitrile, dimethylformamide or toluene), preferably under reflux (cf. also the Preparation Examples) and, if appropriate, reacting the resulting tetrazole derivatives of the formula (VII-A)

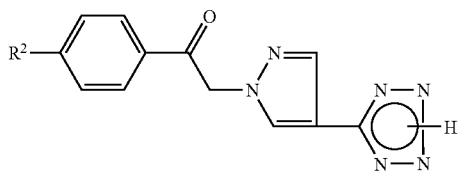

(VII-A)

in which
R² is as defined above
with compounds of the formula (XVII)

E-Y (XVII)

in which
Y has the meanings given above under X⁴ and X⁵, except for hydrogen, and
E represents an anionic leaving group
in the presence of a diluent (for example acetonitrile or dimethylformamide) and, if appropriate, in the presence of an acid acceptor. (for example potassium carbonate) at temperatures between 0° C. and 80° C. (preferably between 20° C. and 50° C.).

The 2-(4-cyanopyrazol-1-yl)acetophenones of the formula (X) to be used as starting materials for carrying out the process (i) according to the invention have already been described above in connection with process (e).

The formula (XVII) provides a general definition of the compounds furthermore to be used as starting materials for carrying out the process (i) according to the invention. In this formula, X⁴ and X⁵ have, in each case with the exception of hydrogen, preferably, particularly preferably, very particularly preferably and especially preferably those meanings which have already been mentioned in connection with the description of the compounds of the formula (I) according to the invention as being preferred, particularly preferred, very particularly preferred and especially preferred for these radicals. E preferably represents chlorine, bromine, iodine, acetoxy, tosyl or mesyl.

Compounds of the formula (XVII) are known and/or can be obtained by known processes.

When preparing compounds in which X⁴ and/or X⁵ represent a tertiary alkyl radical, it is sometimes advantageous to react the compounds of the formula (VII-A) with tertiary alcohols in the presence of strong acids (for example trifluoroacetic acid and/or sulphuric acid) (cf. also the Preparation Examples).

Furthermore, the 2-[4-tetrazolyl-pyrazol-1-yl]acetophenones of the formula (VII f)

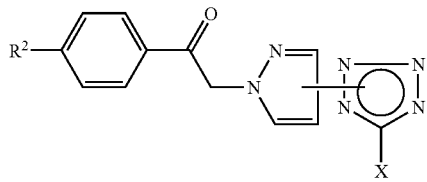

(VIIf)

in which
R² is as defined above and
X has the meanings give above for X⁴ and X⁵
can be obtained, for example, by reacting
j) 2-(4-halopyrazol-1-yl)acetophenones of the formula (XVIII)

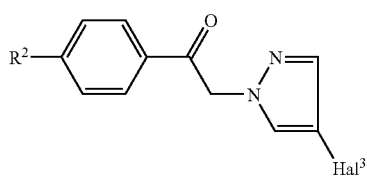

(XVIII)

in which
R² is as defined above and
Hal³ represents halogen
with tetrazoles of the formula (XIX)

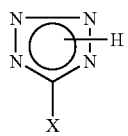

(XIX)

in which
X is as defined above
in the presence of an organic or inorganic base (for example potassium carbonate) and, if appropriate, in the presence of an inert organic solvent (for example acetonitrile or dimethylformamide) at temperatures between 0 and 120° C., preferably between 20° C. and 100° C.

The formula (XVIII) provides a general definition of the 2-(4-halopyrazol-1-yl)-acetophenones to be used as starting materials for carrying out the process (j) according to the invention. In this formula, R² preferably, particularly preferably, very particularly preferably and especially preferably has those meanings which have already been mentioned in connection with the description of the compounds of the formula (I) according to the invention as being preferred, particularly preferred, very particularly preferred and especially preferred for this radical. Hal; preferably represents chlorine, bromine, iodine.

The 2-(4-halopyrazol-1-yl)acetophenones of the formula (XIII) are known and/or can be obtained in a generally known manner.

The formula (XIX) provides a general definition of the tetrazoles further to be used as starting materials for carrying out the process (j) according to the invention. In this formula, X preferably, particularly preferably, very particularly preferably and especially preferably has those meanings which have already been mentioned in connection with the description of the compounds of the formula (I) according to the invention as being in each case preferred, particularly preferred, very particularly preferred and especially preferred for the radicals $X^4$ and $X^5$.

The tetrazoles of the formula (XVIII) are known and/or can be obtained in a generally known manner.

The formula (VIII) provides a general definition of the bis-dialkylaminomethanes further to be used as starting materials for carrying out the process (d) according to the invention. In this formula, Alk preferably represents methyl, ethyl, n-, i-propyl, n-, i-, s- or t-butyl.

Bis-dialkylaminomethanes of the formula (VIII) are known.

The formula (III) provides a general definition of the isocyanates further to be used as starting materials in the process (a) according to the invention. In this formula, $R^3$ preferably, particularly preferably, very particularly preferably and especially preferably has those meanings which have already been mentioned in connection with the description of the compounds of the formula (I) according to the invention as being preferred, particularly preferred, very particularly preferred and especially preferred for this radical.

The isocyanates of the formula (III) are generally known compounds of organic chemistry and/or can be obtained in a generally known manner.

The formula (IV) provides a general definition of the halides to be used as starting materials for carrying out the process (b) according to the invention. In this formula, $R^4$ preferably, particularly preferably, very particularly preferably and especially preferably has those meanings which have already been mentioned in connection with the description of the compounds of the formula (I) according to the invention as being preferred, particularly preferred, very particularly preferred and especially preferred for this radical. Hall preferably represents chlorine or bromine.

The halides of the formula (IV) are generally known compounds of organic chemistry.

The formula (V) provides a general definition of the anilines to be used as starting materials for carrying out the process (c) according to the invention. In this formula, $R^3$ and $R^4$ preferably, particularly preferably, very particularly preferably and especially preferably have those meanings which have already been mentioned in connection with the description of the compounds of the formula (I) according to the invention as being preferred, particularly preferred, very particularly preferred and especially preferred for these radicals.

The anilines of the formula (V) are generally known compounds of organic chemisty and/or can be obtained in a generally known manner.

The process (a) according to the invention is preferably carried out using diluents. Suitable diluents are virtually all inert organic solvents. These preferably include aliphatic and aromatic, optionally halogenated hydrocarbons, such as pentane, hexane, heptane, cyclohexane, petroleum ether, benzine, ligroine, benzene, toluene, xylene, methylene chloride, ethylene chloride, chloroform, carbon tetrachloride, chlorobenzene and o-dichlorobenzene, ethers, such as diethyl ether, dibutyl ether, methyl tert-butyl ether, methyl tert-amyl ether, glycol dimethyl ether, diglycol dimethyl ether, tetrahydrofuran and dioxane, ketones, such as acetone, methyl ethyl ketone, methyl isopropyl ketone or methyl isobutyl ketone, esters, such as methyl acetate or ethyl acetate, nitriles, such as, for example, acetonitrile or propionitrile, amides, such as, for example, dimethylformamide, dimethylacetamide and N-methylpyrrolidone, and also dimethyl sulphoxide, tetramethylene sulphone or hexamethyl phosphoric triamide.

The process (a) according to the invention is preferably also carried out using a catalyst. Suitable catalysts are in particular tertiary organic amines, such as, for example, triethylamine.

In the process (a) according to the invention, the reaction temperatures can be varied within a relatively wide range. In general, the process is carried out at temperatures between 0° C. and 120° C., preferably at temperatures between 20° C. and 80° C.

The process (a) according to the invention is generally carried out under atmospheric pressure. However, it is also possible to operate under elevated or reduced pressure.

For carrying out the process (a) according to the invention, the starting materials are generally employed in approximately equimolar amounts. However, it is also possible to use a relatively small excess of one of the two components employed. Work-up is carried out by customary methods (cf. the Preparation Examples).

The processes (b) and (c) according to the invention are preferably carried out using diluents. Suitable diluents are virtually all inert organic solvents. These preferably include aliphatic and aromatic, optionally halogenated hydrocarbons, such as pentane, hexane, heptane, cyclohexane, petroleum ether, benzine, ligroine, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone or methyl isobutyl ketone, esters, such as methyl acetate or ethyl acetate, nitriles, such as, for example, acetonitrile or propionitrile, amides, such as, for example, dimethylformamide, dimethylacetamide and N-methylpyrrolidone, and also dimethyl sulphoxide, tetramethylene sulphone or hexamethyl phosphoric triamide.

Suitable bases for carrying out the processes (b) and (c) according to the invention are all acid binders which are customarily used for such reactions. Preferred are alkali metal and alkaline earth metal hydrides, such as lithium hydride, sodium hydride, potassium hydride or calcium hydride; alkali metal and alkaline earth metal hydroxides, such as lithium hydroxide, sodium hydroxide, potassium hydroxide or calcium hydroxide; alkali metal and alkaline earth metal carbonates or dicarbonates, such as sodium carbonate, potassium carbonate, sodium bicarbonate, potassium bicarbonate or calcium carbonate; alkali metal acetates, such as sodium acetate or potassium acetate, alkali metal alkoxides, such as sodium tert-butoxide or potassium tert-butoxide; furthermore basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethylaniline, pyridine, 2-methyl-, 3-methyl-, 4-methyl-, 2,4-dimethyl-, 2,6-dimethyl-, 2-ethyl-, 4-ethyl- and 5-ethyl-2-methylpyridine, 1,5-diazabicyclo[4.3.0]non-5-ene (DBN), 1,8-diazabicyclo[5.4.0]undec-7-ene (DBU) and 1,4-diazabicyclo[2.2.2]octane (DABCO).

In the process (b) according to the invention, the reaction temperatures can be varied within a relatively wide range. In general, the process is carried out at temperatures between 0° C. and 120° C., preferably at temperatures between 20° C. and 80° C.

The process (b) according to the invention is generally carried out under atmospheric pressure. However, it is also possible to operate under elevated or reduced pressure.

For carrying out the process (b) according to the invention, the starting materials are generally employed in approximately equimolar amounts. However, it is also possible to employ an excess of halide and base. Work-up is carried out by customary methods.

In the process (c) according to the invention, the reaction temperatures can be varied within a relatively wide range. In general, the process is carried out at temperatures between −10° C. and 120° C., preferably at temperatures between 0° C. and 100° C.

The process (c) according to the invention is generally carried out under atmospheric pressure. However, it is also possible to operate under elevated or reduced pressure.

For carrying out the process (c) according to the invention, the starting materials are generally employed in approximately equimolar amounts. However, it is also possible to employ an excess of chloride and base. Work-up is carried out by customary methods (cf. the Preparation Examples).

The active compounds, having good plant tolerance and favourable warm-blood toxicity, are suitable for controlling animal pests, in particular insects, arachnids and nematodes, which are encountered in agriculture, in forestry, in the protection of stored products and of materials, and in the hygiene sector. They may be preferably used as crop protection agents. They are active against normally sensitive and resistant species and against all or some stages of development. The abovementioned pests include:

From the order of the Isopoda, for example, *Oniscus asellus*, *Armadillidium vulgare* and *Porcellio scaber*.

From the order of the Diplopoda, for example, *Blaniulus guttulatus*.

From the order of the Chilopoda, for example, *Geophilus carpophagus* and *Scutigera* spp.

From the order of the Symphyla, for example, *Scutigerella immaculate*.

From the order of the Thysanura, for example, *Lepisma saccharina*.

From the order of the Collembola, for example, *Onychiurus armatus*.

From the order of the Orthoptera, for example, *Acheta domesticus*, *Gryllotalpa* spp., *Locusta migratoria* migratorioides, *Melanoplus* spp. and *Schistocerca gregaria*.

From the order of the Blattaria, for example, *Blatta orientalis*, *Periplaneta americana*, *Leucophaea maderae* and *Blattella germanica*.

From the order of the Dermaptera, for example, *Forficula auricularia*.

From the order of the Isoptera, for example, *Reticulitermes* spp.

From the order of the Phthiraptera, for example, *Pediculus humanus corporis*, *Haematopinus* spp., *Linognathus* spp., *Trichodectes* spp. and *Damalinia* spp.

From the order of the Thysanoptera, for example, *Hercinothrips femoralis*, *Thrips tabaci*, *Thrips palmi* and *Frankliniella accidentalis*.

From the order of the Heteroptera, for example, *Eurygaster* spp., *Dysdercus intermedius*, *Piesma quadrata*, *Cimex lectularius*, *Rhodnius prolixus* and *Triatoma* spp.

From the order of the Homoptera, for example, *Aleurodes brassicae*, *Bemisia tabaci*, *Trialeurodes vaporariorum*, *Aphis gossypii*, *Brevicoryne brassicae*, *Cryptomyzus ribis*, *Aphis fabae*, *Aphis pomi*, *Eriosoma lanigerum*, *Hyalopterus arundinis*, *Phylloxera vastatrix*, *Pemphigus* spp., *Macrosiphum avenae*, *Myzus* spp., *Phorodon humuli*, *Rhopalosiphum padi*, *Empoasca* spp., *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, *Pseudococcus* spp. and *Psylla* spp.

From the order of the Lepidoptera, for example, *Pectinophora gossypiella*, *Bupalus piniarius*, *Cheimatobia brumata*, *Lithocolletis blancardella*, *Hyponomeuta padella*, *Plutella xylostella*, *Malacosoma neustria*, *Euproctis chrysorrhoea*, *Lymantria* spp., *Bucculatrix thurberiella*, *Phyllocnistis citrella*, *Agrotis* spp., *Euxoa* spp., *Feltia* spp., *Earias insulana*, *Heliothis* spp., *Mamestra brassicae*, *Panolis flammea*, *Spodoptera* spp., *Trichoplusia ni*, *Carpocapsa pomonella*, *Pieris* spp., *Chilo* spp., *Pyrausta nubilalis*, *Ephestia kuehniella*, *Galleria mellonella*, *Tineola bisselliella*, *Tinea pellionella*, *Hofmannophila pseudospretella*, *Cacoecia podana*, *Capua reticulana*, *Choristoneura fumiferana*, *Clysia ambiguella*, *Homona magnanima*, *Tortrix viridana*, *Cnaphalocerus* spp. and *Oulema oryzae*.

From the order of the Coleoptera, for example, *Anobium punctatum*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, *Diabrotica* spp., *Psylliodes chrysocephala*, *Epilachna varivestis*, *Atomaria* spp., *Oryzaephilus surinamensis*, *Anthonomus* spp., *Sitophilus* spp., *Otiorrhynchus sulcatus*, *Cosmopolites sordidus*, *Ceuthorrhynchus assimilis*, *Hypera postica*, *Dermestes* spp., *Trogoderma* spp., *Anthrenus* spp., *Attagenus* spp., *Lyctus* spp., *Meligethes aeneus*, *Ptinus* spp., *Niptus hololeucus*, *Gibbium psylloides*, *Tribolium* spp., *Tenebrio molitor*, *Agriotes* spp., *Conoderus* spp., *Melolontha melolontha*, *Amphimallon solstitialis*, *Costelytra zealandica* and *Lissorhoptrus oryzophilus*.

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster*, *Musca* spp., *Fannia* spp., *Calliphora erythrocephala*, *Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus*, *Oscinella frit*, *Phorbia* spp., *Pegomyia hyoscyarmi*, *Ceratitis capitata*, *Dacus oleae*, *Tipula paludosa*, *Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus*, *Latrodectus mactans*, *Acarus siro*, *Argas* spp., *Ornithodoros* spp., *Dermanyssus gallinae*, *Eriophyes ribis*, *Phyllocoptruta oleivora*, *Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa*, *Panonychus* spp., *Tetranychus* spp., *Hemitarsonemus* spp. and *Brevipalpus* spp.

The plant-parasitic nematodes include, for example, *Pratylenchus* spp., *Radopholus similis*, *Ditylenchus dipsaci*, *Tylenchulus semipenetrans*, *Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

The compounds of the formula (I) according to the invention can be employed with particularly good results for controlling plant-damaging insects, such as, for example, against the larvae of the mustard beetle (*Phaedon cochleariae*) or the caterpillars of the army worm (*Spodoptera frugioerda*).

At certain concentrations or application rates, the compounds according to the invention may, if appropriate, also be used as herbicides and microbicides, for example as fungicides, antimycotics and bactericides. If appropriate, they may also be used as intermediates or precursors for the synthesis of further active compounds.

All plants and plant parts can be treated in accordance with the invention. Plants are to be understood as meaning in the present context all plants and plant populations such as desired and undesired wild plants or crop plants (inclusive of naturally occurring crop plants). Crop plants can be plants which can be obtained by conventional plant breeding and optimization methods or by biotechnological and recombinant methods or by combinations of these methods, inclusive of the transgenic plants and inclusive of the plant cultivars protectable or not protectable by plant breeders' rights. Plant parts are to be understood to mean all aboveground and underground parts and organs of plants, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seeds, also by applying one or more coats.

The active compounds can be converted into the customary formulations, such as solutions, emulsions, wettable powders, suspensions, powders, dusts, pastes, soluble powders, granules, suspension-emulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Suitable Solid carriers are:

for example ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention, as such or in their formulations, can also be used as a mixture with known fungicides, bactericides, acaricides, nematicides, or insecticides, for example to widen the spectrum of activity or to prevent the development of resistance. In many cases, synergistic effects are achieved i.e., the efficacy of the mixture is greater than the efficacy of the individual components.

Suitable mixing partners are, for example, the following compounds:

Fungicides:
aldimorph, ampropylfos, ampropylfos-potassium, andoprim, anilazine, azaconazole, azoxystrobin,
benalaxyl, benodanil, benomyl, benzamacril, benzamacryl-isobutyl, bialaphos, binapacryl, biphenyl, bitertanol, blasticidin-S, bromuconazole, bupirimate, buthiobate,
calcium polysulphide, carpropamide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomoiph, diniconazole, diniconazole-M, dinocap, diphenylamine, dipyrithione, ditalimfos, dithianon, dodemorph, dodine, drazoxolon,
ediphenphos, epoxiconazole, etaconazole, ethirimol, etridiazole,
famoxadon, fenapanil, fenarimol, fenbuconazole, fenfuram, fenhexamide, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
guazatine,
hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, iproralicarb, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipynim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, picoxystrobin, pimaricin, piperalin, polyoxin, poiyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur, quinconazole, quintozene (PCNB), quinoxyfen, sulphur and sulphur preparations, spiroxamines, tebuconazole, tecloftalam, tecnazene, tetcyclacis, tetraconazole, thiabendazole, thicyofen, thifluzamides, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole, uniconazole, validamycin A, vinclozolin, viniconazole, zarilamide, zineb, ziram and also Dagger G,

OK-8705, OK-8801,

α-(1,1-di methylethyl)-β-(2-phenoxyethyl)-1H-1,2,4-triazole-1-ethanol,

α-(2,4-dichlorophenyl)-β-fluoro-β-propyl 1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinol, 2',6'-dibromo-2-methyl-4'-trifluoromethoxy-4'-trifluoromethyl-1,3-thiazole-5-carboxanilide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano-[(1-methyl-2-propynyl)-oxy]-methyl]-benzamide, 3-(1,1-dimethylpropyl)-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholinehydrochloride, ethyl [(4-chlorophenyl)-azo]-cyanoacetate, potassium hydrogen carbonate, methanetetrathiol sodium salt, methyl 1-(2,3-dihydro-2,2-dimethyl 1H-inden-1-yl) 1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-(6-methoxy-3-pyridinyl)-cyclopropanecarboxamide, N-[2,2,2-trichloro-1-[(chloroacetyl)-amino]-ethyl]-benzamide, N-[3-chloro-4,5-bis-(2-propinyloxy)-phenyl]-N'-methoxy-methanimidamide, N-formyl-N-hydroxy-DL-alanine sodium salt, O,O-diethyl (2-(dipropylamino)-2-oxoethyl]-ethylphosphoramidothloate, O-methyl S-phenyl phenylpropylphosphoramidothioate, S-methyl 1,2,3-benzothiadiazole-7-carbothioate, spiro[2H]-1-benzopyrane-2,1'(3'H)-isobenzofuran-3'-one, 4-[(3,4-dimethoxyphenyl)-3-(4-fluorophenyl)-acryloyl]-morpholine.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis, Baculoviruses, Beauveria bassiana, Beauveria tenella*, bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothianidine, cyanophos, cyclopryne, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, dicofol, diflubenzuron, dimethoate, dimethylvinphos, diofenolan, disulfoton, docusat-sodium, dofenapyn,
eflusilanate, emamectin, empenthrin, endosulfan, *Entomopfthora* spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximnate, fenvalerate, fipronil, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, indoxacarb, isazofos, isofenphos, isoxathion, ivermectin,
nuclear polyhedrosis viruses,
lambda-cyhalothrin, lufenuron,
malathion, mecarbam, metaldehyde, methamidophos, *metharhizium anisopliae, metharhizium flavoviride*, methidathion, methiocarb, methoprene, methomyl, methoxyfenozide, metolcarb, metoxadiazone, mevinphos, milbemectin, milbemycin, monocrotophos,
naled, nitenpyram, nithiazine, novaluron,
omethoate, oxamyl, oxydemethon M,
*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propargite, propoxur, prothiofos, prothoate, pymetrozine, pyraclofos, pyresmethrin, pyrethrum, pyridaben, pyridathion, pyrimidifen, pyriproxyfen,
quinalphos,
ribavirin,
salithion, sebufos, silafluofen, spinosad, spirodiclofen, sulfotep, sulprofos,
tau-fluvalinate, tebufenozide, tebufenpyrad, tebupirimiphos, teflubenzuron, tefluthrin, temephos, temivinphos, terbufos, tetrachlorvinphos, tetradifon, thetacypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazurone, trichlophenidine, trichlorfon, triflumuron, trimethacarb,
vamidothion, vaniliprole, *Verticillium lecanii*,
—YI 5302,
zeta-cypermethrin, zolaprofos,
(1R-cis)-[5-(phenylmethyl)-3-furanyl]-methyl 3-[(dihydro-2-oxo-3(2H)-furanylidene)-methyl]-2,2-dimethylcyclopropanecarboxylate,
(3-phenoxyphenyl)-methyl 2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]-4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate,
4-[4-(4-ethoxyphenyl)-4-methylpentyl]-1-fluoro-2-phenoxy-benzene,
4-chloro-2-(1,1-dimethylethyl)-5-[[2-(2,6-dimethyl-4-phenoxyphenoxy)ethyl]thiol]-3(2H)-pyridazinone,
4-chloro-2-(2-chloro-2-methylpropyl)-5-[(6-iodo-3-pyridinyl)methoxy]-3(2H)-pyrida
4-chloro-5-[(6-chloro-3-pyridinyl)methoxy]-2-(3,4-dichlorophenyl)-3(2H)-pyridazinone,
*Bacillus thuringiensis* strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5]dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde,
ethyl [2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]4,5-dihydro-4-phenyl 1H-pyrazole-1-carboxamide,
N-[(2-chloro-5-thiazolyl)methyl]-N'-methyl-N"-nitro-guanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl [2-(dipropylamino)-2-oxoethyl]-ethylphosphoramidothioate,
N-cyanomethyl-4-trifluoromethyl-nicotinamide,
3,5-dichloro-1-(3,3-dichloro-2-propenyloxy)-4-[3-(5-trifluoromethylpyridin-2-yloxy)propoxy]-benzene.

A mixture with other known active compounds, such as herbicides, or with fertilizers and growth regulators is also possible.

The active compounds according to the invention can furthermore be present when used as insecticides in their commercially available formulations and in the use forms prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. This can be varieties, bio- and genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageously useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapevines), and particular emphasis is given to maize, soya beans, potatoes, cotton and oilseed rape. Traits that are emphasized are in particular increased defence of the plants against insects by toxins formed in the plants, in particular those formed by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants to fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still-to-be-developed genetic traits, which plants will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or the mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattela germanica* and *Supella* spp.

From the subclass of the Ac aria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Larminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injections (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as being preferred—but without any limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec. and *Dinoderus minutus.*

Hymenopterons, such as

*Sirex juvencus, Urocerus gigas, Urocerus gigas taignus* and *Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus.*

Bristletails, such as *Lepisma saccharina.*

Industrial materials in the present context are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agent according to the invention or mixtures comprising this are to be understood as meaning, for example:

building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyes and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be protected.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 450°. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., turpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can at the same time be employed for protecting objects which come into contact with salt water or brackish water, in particular hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpelluin* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis-(trialkyltin) sulphides, tri-n-butyltin laurate, tri-n-butyltin chloride, copper(I) oxide, triethyltin chloride, tri-n-butyl-(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combination with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as
benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacarb;
or conventional antifouling active compounds such as
4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as rosin to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests alone or in combination with other active compounds and auxiliaries. They are active against sensitive and resistant species and against all development stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus* and *Dermatophagoildes forinae*.

From the order of the Araneae, for example, *Aviculariidae* and *Araneidae*.

From the order of the Opiliones, for example, *Pseudoscorpiones chelifer, Pseudoscorpiones cheiridium* and *Opiliones phalangium*.

From the order of the Isopoda, for example, *Oniscus asellus* and *Porcellio scaber*.

From the order of the Diplopoda, for example, *Blaniulus guttulatus* and *Polydesmus* spp.

From the order of the Chilopoda, for example, *Geophilus* spp.

From the order of the Zygentoma, for example, *Ctenolepisma* spp., *Lepisma saccharina* and *Lepismodes inquilinus*.

From the order of the Blattaria, for example, *Blatta orientalies, Blattella germanica, Blattella asahiniai, Leucophaea maderae, Panchlora* spp., *Parcoblatta* spp., *Periplaneta australasiae, Periplaneta americana, Periplaneta brunnea, Periplaneta fuliginosa* and *Supella longipalpa*.

From the order of the Saltatoria, for example, *Acheta domesticus*.

From the order of the Dermaptera, for example, *Forficula auricularia*.

From the order of the Isoptera, for example, *Kalotermes* spp. and *Reticulitermes* spp.

From the order of the Psocoptera, for example, *Lepinatus* spp. and *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais* and *Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans* and *Tipula paludosa*.

From the order of the Lepidoptera, for example, *Achroia grisella, Galleria mellonella, Plodia interpunctella, Tinea cloacella, Tinea pellionella* and *Tineola bisselliella*.

From the order of the Siphonaptera, for example, *Ctenocephalides canis, Ctenocephalides felis, Pulex irritans, Tunga penetrans* and *Xenopsylla cheopis*.

From the order of the Hymenoptera, for example, *Camponotus herculeanus, Lasius fuliginosus, Lasius niger, Lasius umbratus, Monomorium pharaonis, Paravespula* spp. and *Tetramorium caespitum*.

From the order of the Anoplura, for example, *Pediculus humanus capitis, Pediculus humanus corporis* and *Phthirus pubis*.

From the order of the Heteroptera, for example, *Cimex hernipterus, Cimex lectularius, Rhodnius prolixus* and *Triatoma infestans*.

They are used in the household insecticides sector alone or in combination with other suitable active compounds such as phosphoric esters, carbamates, pyrethroids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

PREPARATION EXAMPLES

Example 1

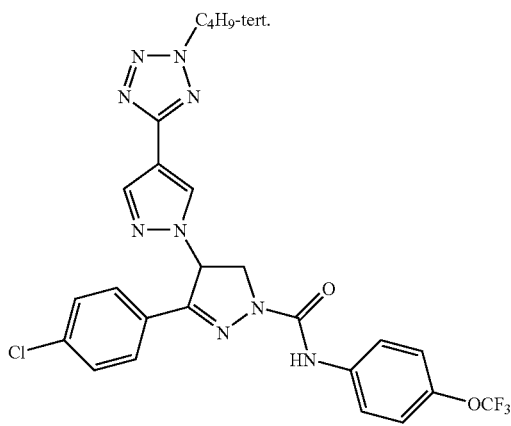

(Process a)

At 70° C., 0.6 g (3 mmol) of 4-trifluoromethoxyphenyl isocyanate is added to a mixture of 1.1 g (3 mmol) of 3-(4-chlorophenyl)-4-[4-(2-tert-butyltetrazol-5-yl)pyrazol-1-yl]-4,5-dihydro-1H-pyrazole, 0.1 ml of triethylamine and 50 ml of methyl-tert-amyl ether. The mixture is stirred at 70° C. for 15 minutes and then allowed to cool slowly to room temperature. The solvent is then distilled off under reduced pressure and the residue is purified by silica gel chromatography (methylene chloride/diethyl ether 5:1).

This gives 1.1 g (64% of theory) of N-(4-trifluoromethoxy)-3-(4-chlorophenyl)-4-[4-(2-tert-butyltetrazol-5-yl)pyrazol-1-yl]-4,5-dihydro-1-pyrazolecarboxanilide of logP (pH 2)=4.63.

Preparation of the Starting Material (II-1)

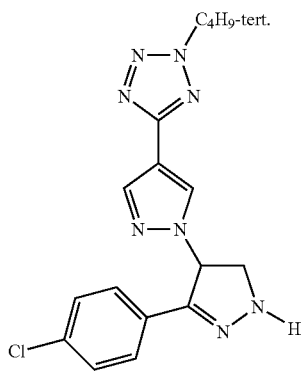

At room temperature, 1.5 g (0.015 mol) of bis-dimethylaminomethane are added to a solution of 4.9 g (0.014 mol) of 2-[4-(2-tert-butyltetrazol-5-yl)pyrazol-1-yl]4'-chloroacetophenone in 50 ml of methylene chloride, and the mixture is boiled under reflux for 18 hours. The solvent is then distilled off under reduced pressure and the residue is dissolved in 50 ml of ethanol. 0.8 g (0.016 mol) of hydrazine hydrate is added, and the reaction mixture is then stirred at 30° C. for 3 hours. About 200 ml of water are then added, and the precipitated product is filtered off with suction.

This gives 3.6 g (61% of theory) of 3-(4-chlorophenyl)-4-[4-(2-tert-butyltetrazol-5-yl)pyrazol-1-yl]4,5-dihydro-1H-pyrazole of logP (pH 2)=2.91.

Preparation of the Precursor (VII-1)

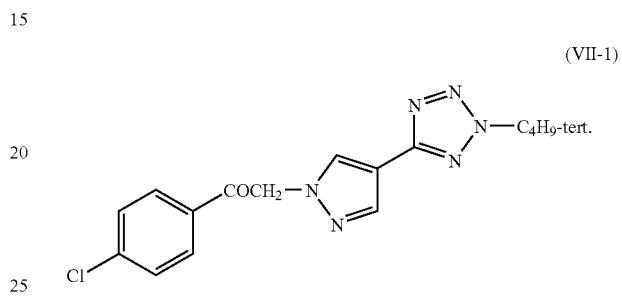

A mixture of 4.3 g (0.015 mol) of 2-[4-(tetrazol-5-yl)pyrazol-1-yl]-4'-chloroacetophenone, 6.8 g of tert-butanol, 0.8 g of conc. sulphuric acid and 60 ml of trifluoroacetic acid is stirred at room temperature for 16 hours. The solvent is then distilled off under reduced pressure, about 100 ml of water are added to the residue and the mixture is neutralized using sodium bicarbonate. The precipitated product is filtered off with suction and washed with water.

This gives 4.9 g (95% of theory) of 2-[4-(2-tert-butyltetrazol-5-yl)pyrazol-1-yl]-4'-chloroacetophenone in the form of colourless crystals of logP (pH 2)=2.96.

(VII-2)

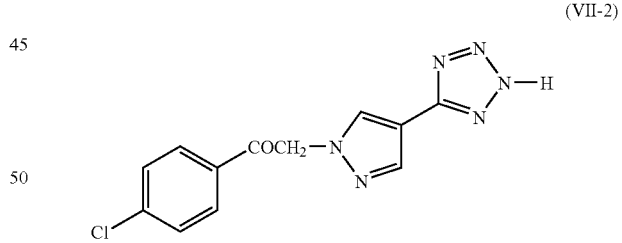

A mixture of 14.75 g (0.06 mol) of 2-(4-cyanopyrazol-1-yl)-4'-chloroacetophenone, 17.4 g (0.126 mol) of triethylamine hydrochloride, 8.4 g (0.126 mol) of sodium azide and 100 ml of toluene is boiled under reflux for 16 hours. The solvent is then distilled off under reduced pressure, the residue is dissolved in 200 ml of about 5% strength aqueous sodium hydroxide solution and insoluble particles are filtered off. The filtrate is adjusted to about pH 2 using dilute hydrochloric acid and the precipitated product is then filtered off and washed with water.

This gives 15.3 g (88% of theory) of 2-[4-(tetrazol-5-yl)pyrazol-1-yl]-4'-chloroacetophenone of logP (pH 2)=1.60.

Example 2

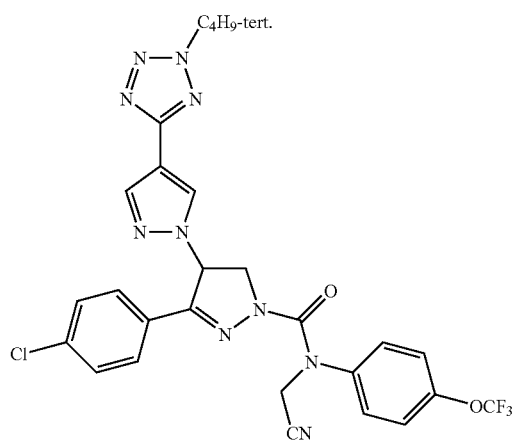

(Process c)

At 0° C., 1 g (3.6 mmol) of N-cyanomethyl-N-(4-trifluoromethoxy)phenylcarbamoyl chloride is added dropwise to a solution of 1.1 g (3 mmol) of 3-(4-chlorophenyl)-4-[4-(2-tert-butyltetrazol-5-yl)pyrazol-1-yl]-4,5-dihydro-1H-pyrazole [Ex. II-1] and 0.5 ml (3.6 mmol) of triethylamine in 30 ml of methylene chloride, and the mixture is stirred at room temperature for 48 hours. The mixture is washed twice with in each case 100 ml of water and the organic phase is dried over sodium sulphate and concentrated under reduced pressure. The residue is purified by silica gel chromatography (methylene chloride/diethyl ether=10:1).

This gives 1.1 g (61% of theory) of N-cyanomethyl-N(4-trifluoromethoxy)-3-(4-chlorophenyl)-4-[4-(2-tert-butyltetrazol-5-yl)pyrazol-1-yl]-4,5-dihydro-1-pyrazolecarboxanilide of logP (pH 2)=4.40.

Preparation of the Starting Material

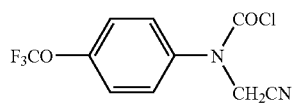

(VI-1)

At 0° C., a solution of 20.7 g (0.0958 mol) of N-cyanomethyl-4-trifluoromethoxyaniline and 11.6 g (0.115 mol) of triethylamine in 150 ml of toluene is added dropwise to a solution of 10.4 g (0.105 mol) of phosgene in 100 ml of toluene, and the mixture is stirred at room temperature for 18 hours. Excess phosgene

TABLE 1

(I)

Structure shown with substituents $R^1$, $R^2$, $R^3$, $R^4$ on a pyrazole-carboxanilide scaffold.

| Ex. No. | $R^1$ | $R^2$ | $R^3$ | $R^4$ | logP (pH 2) |
|---|---|---|---|---|---|
| 3 | 2-tert-butyl-tetrazol-5-yl (CH$_3$), C$_4$H$_9$-tert. | Cl | SCF$_3$ | H | 4.99 |
| 4 [a] | 2-methyl-tetrazol-5-yl, CH$_3$ | Cl | OCF$_3$ | H | 3.75 |
| 5 [b] | 2-methyl-tetrazol-5-yl, CH$_3$ | Cl | SCF$_3$ | H | 4.12 |
| 6 | 2-methyl-tetrazol-5-yl, CH$_3$ | Cl | OCF$_3$ | CH$_2$CN | 3.51 |
| 7 [a] | 1-methyl-tetrazol-5-yl, CH$_3$ | Cl | OCF$_3$ | H | 3.45 |
| 8 [b] | 1-methyl-tetrazol-5-yl, CH$_3$ | Cl | SCF$_3$ | H | 3.79 |
| 9 | 2-tert-butyl-tetrazol-5-yl, C$_4$H$_9$-tert. | Cl | SCF$_3$ | CH$_2$CN | |
| 10 | 2-methyl-tetrazol-5-yl, CH$_3$ | Cl | SCF$_3$ | CH$_2$CN | |
| 11 | 2-tert-butyl-tetrazol-5-yl, C$_4$H$_9$-tert. | Cl | Cl | H | |
| 12 | 2-tert-butyl-tetrazol-5-yl, C$_4$H$_9$-tert. | Cl | CF$_3$ | H | |
| 13 | 2-ethyl-tetrazol-5-yl, C$_2$H$_5$ | Cl | OCF$_3$ | H | |

TABLE 1-continued (I)

R¹ = substituent on pyrazole; structure: pyrazole-N connected to pyrazoline C4; pyrazoline C3 has phenyl bearing R², pyrazoline N1 has C(=O)-N(R⁴)-phenyl-R³

| Ex. No. | R¹ | R² | R³ | R⁴ | logP (pH 2) |
|---|---|---|---|---|---|
| 14 | 3-methyl-5-tert-butyl-1,2,4-oxadiazol-... (N=C(CH₃)-O-N=C(C₄H₉-tert)) | Cl | OCF₃ | H | |
| 15 | methyl/CF₃ oxadiazole isomer | Cl | OCF₃ | H | |
| 16 | methyl/C₄H₉-tert oxadiazole isomer | Cl | OCF₃ | H | |
| 17 | methyl/CF₃ oxadiazole isomer | Cl | OCF₃ | H | |
| 18 | methyl/C₄H₉-tert oxadiazole | Cl | SCF₃ | H | |
| 19 | methyl/C₄H₉-tert oxadiazole | Cl | OCF₃ | CH₂CN | |
| 20 | methyl/C₄H₉-tert oxadiazole | Cl | SCF₃ | CH₂CN | |
| 21 | methyl/CF₃ oxadiazole | Cl | OCF₃ | CH₂CN | |
| 22 | methyl/C₄H₉-tert oxadiazole | Cl | OCF₃ | CH₂CN | |
| 23 | methyl/CF₃ oxadiazole | Cl | OCF₃ | CH₂CN | |
| 24 | methyl/C₄H₉-tert oxadiazole | Cl | SCF₃ | H | | a) Compounds 4 and 7 are obtained as a mixture of isomers and are biologically tested as such (see Use Examples).

b) Compounds 5 and 8 are obtained as a mixture of isomers and are biologically tested as such (see Use Examples).

The compounds of the formula (II) listed in Table 2 below can be obtained analogously to Example 1 and/or in accordance with the general statements on the preparation:

TABLE 2

(II)

| Ex. No. | R¹ | R² | logP (pH 2) |
|---|---|---|---|
| 11-2 | 2-methyl-5-methyl-tetrazol-yl (N-N(CH₃), N=N, CH₃) | Cl | 1.94 |
| 11-3 | 1-methyl-5-methyl-tetrazol-yl | Cl | 1.69 |
| 11-4 | 2-ethyl-5-methyl-tetrazol-yl (C₂H₅) | Cl | |
| 11-5 | methyl/C₄H₉-tert 1,2,4-oxadiazole | Cl | |
| 11-6 | methyl/CF₃ 1,2,4-oxadiazole | Cl | |
| 11-7 | methyl/C₄H₉-tert 1,2,4-oxadiazole | Cl | |

TABLE 2-continued

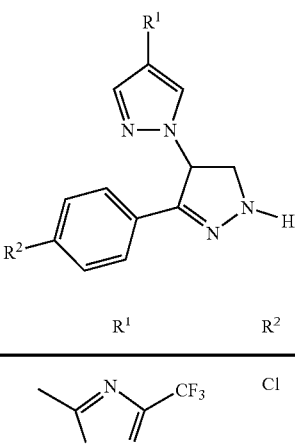

(II)

| Ex. No. | R¹ | R² | logP (pH 2) |
|---|---|---|---|
| 11-8 | (5-methyl-3-trifluoromethyl-1,2,4-oxadiazol-yl) | Cl | |

The compounds of the formula (VII) listed in Table 3 below can be obtained analogously to Example 2 and/or in accordance with the general statements on the preparation:

TABLE 3

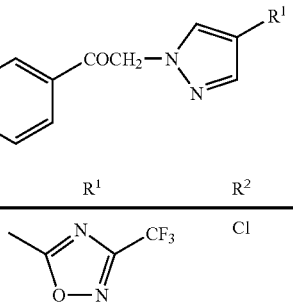

(VII)

| Ex. No. | R¹ | R² | logP (pH 2) |
|---|---|---|---|
| VII-3 | (1-methyl-4-methyl-tetrazolyl) | Cl | 2.05 |
| VII-4 | (tetrazolyl-CH₃) | Cl | 1.80 |
| VII-5 | (tetrazolyl-C₂H₅) | Cl | |
| VII-6 | (methyl-C₄H₉-tert oxazole) | Cl | |
| VII-7 | (methyl-CF₃ oxazole) | Cl | |
| VII-8 | (methyl-C₄H₉-tert oxadiazole) | Cl | |

TABLE 3-continued (VII)

| Ex. No. | R¹ | R² | logP (pH 2) |
|---|---|---|---|
| VII-9 | (methyl-CF₃ oxadiazole) | Cl | |

The logP values given in the Tables and Preparation Examples above are determined in accordance with EEC Directive 79/831 Annex V.A8 by HPLC (High Performance Liquid Chromatography) using a reversed-phase column (C 18). Temperature: 43° C.

The determination is carried out in the acidic range at pH 2.3 using the-mobile phases 0.1% aqueous phosphoric acid and acetonitrile; linear gradient from 10% acetonitrile to 90% acetonitrile.

Calibration is carried out using unbranched alkan-2-ones (of 3 to 16 carbon atoms) with known logP values (determination of the logP values by the retention times using linear interpolation between two successive alkanones).

Use Examples

Example A

Phaedon Larvae Test

Solvent: 7 parts by weight of dimethylformamide

Emulsifier: 2 parts by weight of alkylaryl polyglycol ether

To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the following compounds of the Preparation Examples show good activity:

TABLE A
plant-damaging insects
Phaedon Larvae Test
| No. | Active compounds | Concentration of active compound in ppm | Efficacy in % after 7$^d$ |
|---|---|---|---|
| 2 | 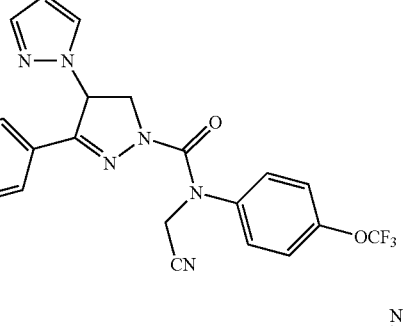 | 500 | 100 |
| 4, 7 | 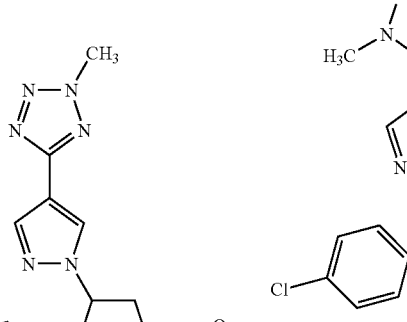 | 500 | 100 |
| 5, 8 | 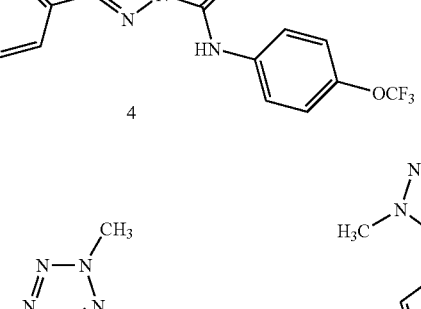 | 500 | 100 |

TABLE A-continued plant-damaging insects
Phaedon Larvae Test

| No. | Active compounds | Concentration of active compound in ppm | Efficacy in % after 7$^d$ |
|---|---|---|---|
| 6 | 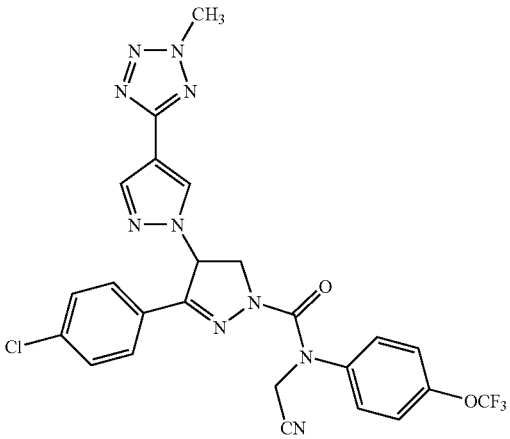 | 500 | 100 |

Example B

*Spodoptera frugiperda* Test
Solvent: 7 parts by weight of dimethylformamide
Emulsifier: 2 parts by weight of alkylaryl polyglycol ether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the army worm (*Spodoptera frugiperda*) while the leaves are still moist.

After the desired period of time, the kill in % is determined. 100% means that all caterpillars have been killed; 0% means that none of the caterpillars have been killed.

In this test at an exemplary active compound concentration of 500 ppm, the compounds 2, 4, 5 and 8 of the Preparation Examples, for example, show a kill of 100% after 7 days.

TABLE B plant-damaging insects
*Spodoptera frugiperda* Test

| No. | Active compounds | Concentration of active compound in ppm | Efficacy in % after 7$^d$ |
|---|---|---|---|
| 2 | 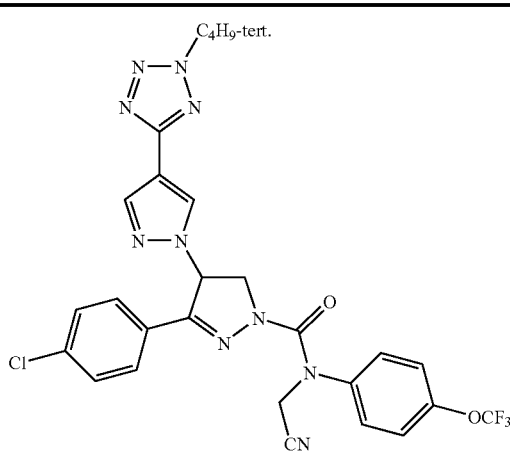 | 500 | 100 |

TABLE B-continued
plant-damaging insects
*Spodoptera frugiperda* Test
| No. | Active compounds | Concentration of active compound in ppm | Efficacy in % after 7ᵈ |
|---|---|---|---|
| 4 | 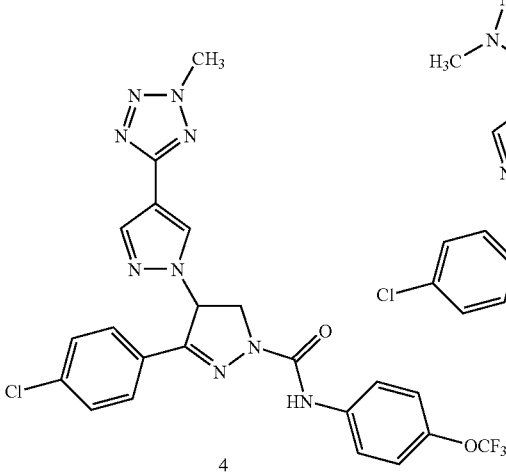 4 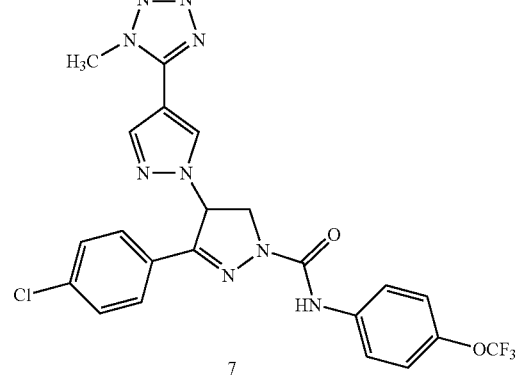 7 | 500 | 100 |
| 5, 8 | 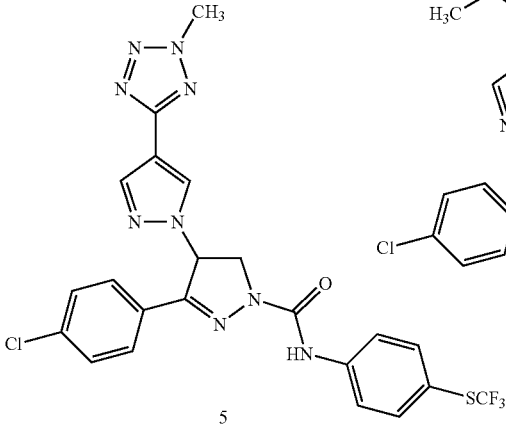 5 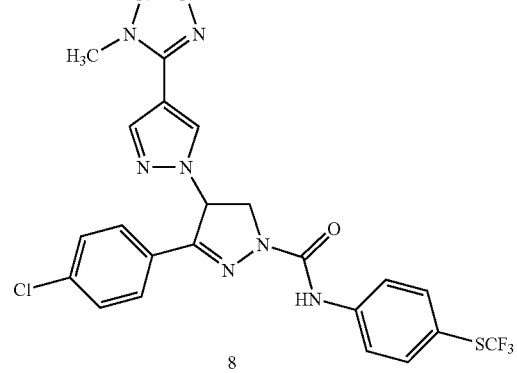 8 | 500 | 100 |
| 14 | 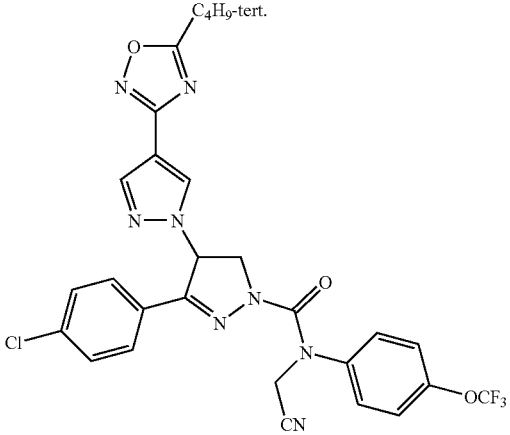 | 500 | 100 |

TABLE B-continued plant-damaging insects
*Spodoptera frugiperda* Test

| No. | Active compounds | Concentration of active compound in ppm | Efficacy in % after 7$^d$ |
|---|---|---|---|
| 18 | [structure: 3-(5-tert-butyl-1,2,4-oxadiazol-3-yl)-pyrazole linked to 4,5-dihydropyrazole with 4-chlorophenyl, N-carbonyl-N-(cyanomethyl)-4-(trifluoromethylthio)aniline] | 500 | 100 |
| 6 | [structure: 5-(2-methyl-2H-tetrazol-5-yl)-pyrazole linked to 4,5-dihydropyrazole with 4-chlorophenyl, N-carbonyl-N-(cyanomethyl)-4-(trifluoromethoxy)aniline] | 500 | 100 |

Example C

*Diabrotica balteata* Test (Larvae in Soil)

Critical Concentration Test/Soil Insects—Treatment of Transgenic Plants

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent, the stated amount of emulsifier is added, and the concentrate is diluted with water to the desired concentration.

The preparation of active compound is mixed intimately with the soil. Here, the concentration of active compound in the preparation is virtually immaterial, only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trademark of Monsanto Comp., USA) are placed into each pot. After 2 days, the appropriate test insects are placed into the treated soil. After a further 7 days, the efficacy of the active compound is determined by counting the maize plants that have emerged (1 plant=20% activity).

Example D

*Heliothis virescens* Test—Treatment of Transgenic Plants
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soyabean shoots (*Glycine max*) of the cultivar Roundup Ready (trademark of Monsanto Comp., USA) are treated by being dipped into the preparation of active compound of the desired concentration and are populated with the, tobacco budworm *Heliothis virescens* while the leaves are still moist.

After the desired period of time, the kill of the insects is determined. 100% means that all caterpillars have been killed; 0% means that none of the caterpillars have been killed.

What is claimed is:

1. A 4-pyrazolylpyrazoline of formula (I)

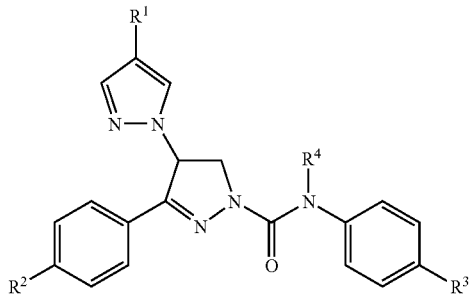

in which
R$^1$ represents optionally substituted hetaryl,
R$^2$ represents halogen, haloalkyl, alkoxy, haloalkoxy, alkylthio, haloalkylthio, alkylsulphonyl, haloalkylsulphinyl, haloalkylsulphonyl, or cyano,
R$^3$ represents halogen, haloalkyl, alkoxy, haloalkoxy, alkylthio, haloalkylthio, haloalkylsulphinyl, haloalkylsulphonyl, or cyano, and
R$^4$ represents hydrogen, cyanomethyl, or alkoxycarbonyl.

2. A 4-pyrazolylpyrazoline of formula (I) according to claim 1 in which
R$^1$ represents oxadiazolyl or thiadiazolyl, each of which is optionally monosubstituted with optionally substituted alkyl, optionally substituted alkoxy, optionally substituted alkylthio, optionally substituted aryl, or optionally substituted arylalkyl; or represents optionally monosubstituted tetrazolyl, wherein the substituents are optionally substituted alkyl, optionally substituted alkylthio or alkylsulphonyl, optionally substituted aryl or arylalkyl, or optionally substituted cycloalkyl,
R$^2$ represents fluorine, chlorine, bromine, iodine, C$_1$-C$_4$-haloalkyl, C$_1$-C$_4$-alkoxy, C$_1$-C$_4$-haloalkoxy, C$_1$-C$_4$-alkylthio, C$_1$-C$_4$-haloalkylthio, C$_1$-C$_4$-alkylsulphonyl, C$_1$-C$_4$-haloalkylsulphinyl, C$_1$-C$_4$-haloalkylsulphonyl, or cyano,
R$^3$ represents fluorine, chlorine, bromine, iodine, C$_1$-C$_4$-haloalkyl, C$_1$-C$_4$-alkoxy, C$_1$-C$_4$-haloalkoxy, C$_1$-C$_4$-alkylthio, C$_1$-C$_4$-haloalkylthio, C$_1$-C$_4$-haloalkylsulphinyl, C$_1$-C$_4$-haloalkylsulphonyl, or cyano, and
R$^4$ represents hydrogen, cyanomethyl, or C$_1$-C$_4$-alkoxycarbonyl.

3. A 4-pyrazolylpyrazoline of formula (I) according to claim 1 in which
R$^1$ represents oxadiazolyl or thiadiazolyl, each of which is optionally monosubstituted with C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio, or C$_1$-C$_4$-haloalkylthio, or with phenyl or benzyl, each of which is optionally mono- to trisubstituted by identical or different substituents selected from the group consisting of halogen, C$_1$-C$_4$-haloalkyl, and C$_1$-C$_4$-haloalkoxy; or represents optionally monosubstituted tetrazolyl, wherein the substituents are C$_1$-C$_4$-alkyl, C$_1$-C$_4$-haloalkyl, C$_1$-C$_4$-alkylthio, or C$_1$-C$_4$-alkylsulphonyl, or are phenyl or benzyl, each of which is optionally mono- to trisubstituted by identical or different substituents selected from the group consisting of halogen, C$_1$-C$_4$-haloalkyl, and C$_1$-C$_4$-haloalkoxy, or are cyclopentyl or cyclohexyl, each of which is optionally mono- to trisubstituted by identical or different C$_1$-C$_4$-alkyl,
R$^2$ represents fluorine, chlorine, bromine, iodine, cyano, C$_1$-C$_2$-alkylthio, or C$_1$-C$_4$-alkylsulphonyl; or represents C$_1$-C$_2$-haloalkyl, C$_1$-C$_2$-haloalkoxy, C$_1$-C$_2$-haloalkylthio, or C$_1$-C$_2$-haloalkylsulphonyl having in each case 1 to 5 identical or different halogen atoms selected from the group consisting of fluorine, chlorine, and bromine,
R$^3$ represents chlorine, bromine, iodine, or cyano; or represents C$_1$-C$_2$-haloalkyl, C$_1$-C$_2$-haloalkoxy, C$_1$-C$_2$-haloalkylthio, C$_1$-C$_2$-haloalkylsulphinyl, or C$_1$-C$_2$-haloalkylsulphonyl having in each case 1 to 5 identical or different halogen atoms selected from the group consisting of fluorine, chlorine, and bromine, and
R$^4$ represents hydrogen, cyanomethyl, or C$_1$-C$_4$-alkoxycarbonyl.

4. A 4-pyrazolylpyrazoline of formula (I) according to claim 1 in which
R$^1$ represents an oxadiazolyl group selected from the group consisting of:

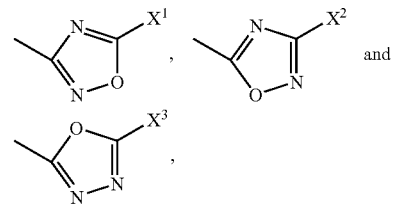

where X$^1$, X$^2$, and X$^3$ independently of one another represent hydrogen, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio, or C$_1$-C$_4$-haloalkylthio; or represent phenyl or benzyl, each of which is optionally mono- to trisubstituted by identical or different substituents selected from the group consisting of halogen, C$_1$-C$_2$-haloalkyl, and C$_1$-C$_2$-haloalkoxy having in each case 1 to 3 identical or different halogen atoms selected from the group consisting of fluorine, chlorine, and bromine; or
represents a tetrazolyl group selected from the group consisting of:

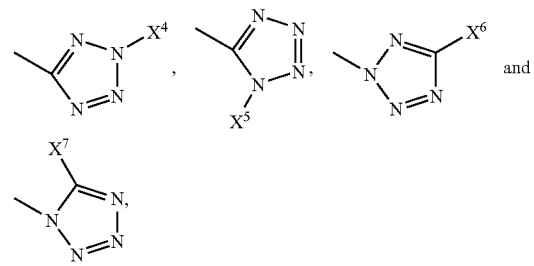

where X$^4$, X$^5$, X$^6$, and X$^7$ independently of one another represent hydrogen or C$_1$-C$_4$-alkyl; represent C$_1$-C$_2$-haloalkyl having 1 to 3 identical or different halogen atoms selected from the group consisting of fluorine, chlorine, and bromine; represent C$_1$-C$_4$-alkylthio or C$_1$-C$_4$-alkylsulphonyl; represent phenyl or benzyl, each of which is optionally mono- to trisubstituted by identical or different substituents selected from the group consisting of halogen, $C_1$-$C_2$-haloalkyl, and $C_{1-2}$-haloalkoxy having in each case 1 to 3 identical or different halogen atoms selected from the group consisting of fluorine, chlorine, and bromine; or represent cyclopentyl or cyclohexyl, each of which is optionally mono- to trisubstituted by identical or different $C_1$-$C_4$-alkyl, $R^2$ represents fluorine, chlorine, bromine, iodine, methylthio, trifluoromethyl, trifluoromethoxy, or trifluoromethylthio, $R^3$ represents chlorine, bromine, iodine, cyano; trifluoromethyl, trifluoromethoxy, trifluoromethylthio, trifluoromethylsulphinyl, or trifluoromethylsulphonyl, and $R^4$ represents hydrogen, cyanomethyl, methoxycarbonyl, ethoxycarbonyl, n- or i-propoxycarbonyl, or n-, i-, s-, or t-butoxycarbonyl.

5. A 4-pyrazolylpyrazoline of formula (I) according to claim 1 in which $R^1$ represents an oxadiazolyl group selected from the group consisting of:

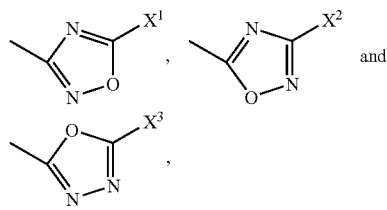

where $X^1$, $X^2$ and $X^3$ independently of one another represent hydrogen, methyl, ethyl, n- or i-propyl, n-, i-, s-, or t-butyl, trifluoromethyl, trifluoromethoxy, or trifluoromethylthio; or represent phenyl or benzyl, each of which is optionally mono- or disubstituted by identical or different substituents selected from the group consisting of fluorine, chlorine, bromine, trifluoromethyl, and trifluoromethoxy; or represents a tetrazolyl group from the group consisting of:

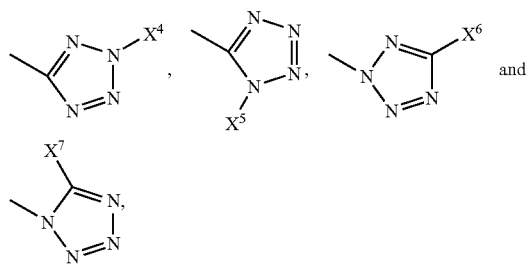

where $X^4$, $X^5$, $X^6$ and $X^7$ independently of one another represent hydrogen, methyl, ethyl, n- or i-propyl, n-, i-, s-, or t-butyl; fluoromethyl, difluoromethyl, trifluoromethyl, 1,1-difluoroethyl, 2,2,2-trifluoroethyl, methylthio, ethylthio, methylsulphonyl, or ethylsulphonyl; represent phenyl or benzyl, each of which is optionally mono- or disubstituted by identical or different substituents selected from the group consisting of fluorine, chlorine, bromine, trifluoromethyl, and trifluoromethoxy; or represent cyclohexyl that is optionally mono- or disubstituted by methyl, $R^2$ represents fluorine, chlorine, bromine, iodine, or trifluoromethylthio, $R^3$ represents chlorine, bromine, iodine, cyano, trifluoromethyl, trifluoromethoxy, trifluoromethylthio, trifluoromethylsulphinyl, or trifluoromethylsulphonyl, and $R^4$ represents hydrogen or cyanomethyl.

6. A 4-pyrazolylpyrazoline of formula (I) according to claim 1 in which $R^2$ represents halogen.

7. A 4-pyrazolylpyrazoline of formula (I) according to claim 1 in which $R^2$ represents fluorine, chlorine, bromine, or iodine.

8. A 4-pyrazolylpyrazoline of formula (I) according to claim 1 in which $R^2$ represents fluorine or chlorine.

9. A 4-pyrazolylpyrazoline of formula (I) according to claim 1 in which $R^2$ represents chlorine.

10. A 4-pyrazolylpyrazoline of formula (I) according to claim 1 in which $R^3$ represents fluorine, chlorine, bromine, iodine, or cyano; or represents $C_1$-$C_2$-haloalkyl, $C_1$-$C_2$-haloalkoxy, $C_1$-$C_2$-haloalkylthio, $C_1$-$C_2$-haloalkylsulphinyl, or $C_1$-$C_2$-haloalkylsulphonyl having in each case 1 to 5 identical or different halogen atoms selected from the group consisting of fluorine, chlorine, and bromine.

11. A 4-pyrazolylpyrazoline of formula (I) according to claim 1 in which $R^3$ represents chlorine, trifluoromethyl, trifluoromethoxy, or trifluoromethylthio.

12. A 4-pyrazolylpyrazoline of formula (I) according to claim 1 in which $R^4$ represents hydrogen or cyanomethyl.

13. A 4-pyrazolylpyrazoline of formula (I) according to claim 1 in which $R^2$ represents chlorine and $R^4$ represents hydrogen or cyanomethyl.

14. A process for preparing a 4-pyrazolylpyrazoline of formula (I) according to claim 1 comprising (a) reacting a pyrazoline of formula (II)

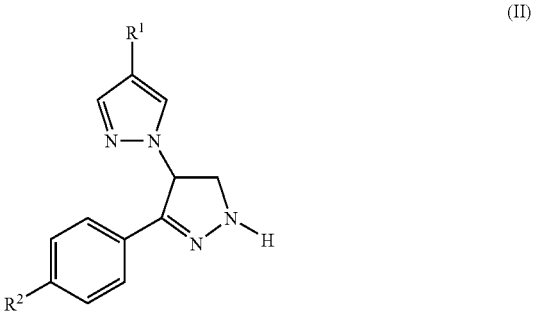

in which $R^1$ and $R^2$ are as defined for formula (I) in claim 1, with an isocyanate of formula (III)

in which $R^3$ is as defined for formula (I) in claim 1, optionally in the presence of a diluent and optionally in the presence of a catalyst, thereby forming a pyrazoline derivative of formula (Ia)

(Ia)

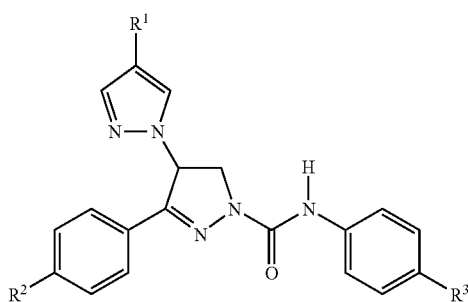

in which R¹, R², and R³ are as defined for formula (I) in claim 1; and
(b) optionally reacting the pyrazoline derivative of formula (Ia) with a halide of the formula (IV)

  (IV)

in which
R⁴ is as defined for formula (I) in claim 1, and
Hal¹ represents halogen,
optionally in the presence of a diluent and optionally in the presence of a base; or
(c) initially reacting an aniline of formula (V)

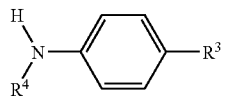  (V)

in which R³ and R⁴ are as defined for formula (I) in claim 1, with phosgene in the presence of a diluent and, optionally, in the presence of a base, to form a carbamoyl chloride of formula (VI)

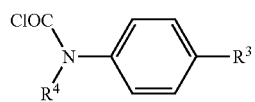  (VI)

in which R³ and R⁴ are as defined for formula (I) in claim 1, and reacting the resultant carbamoyl chloride of formula (VI), directly or after isolation, with a pyrazoline of formula (II)

(II)

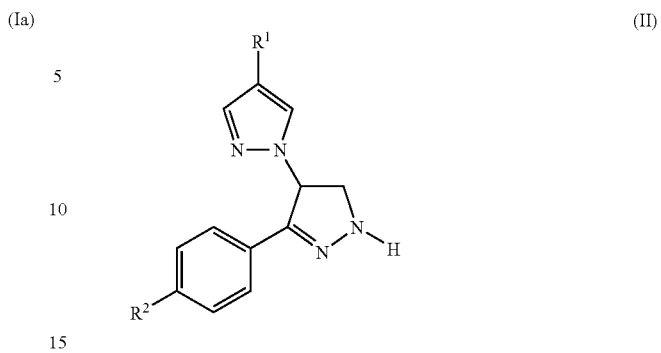

in which R¹ and R² are as defined for formula (I) in claim 1, in the presence of a diluent and, optionally, in the presence of a base.

15. A pesticide comprising one or more 4-pyrazolylpyrazolines of formula (I) according to claim 1 and one or more extenders and/or surfactants.

16. A method for controlling pests comprising allowing an effective amount of a 4-pyrazolylpyrazolines of formula (I) according to claim 1 to act on pests and/or their habitat.

17. A process for preparing pesticides comprising mixing one or more 4-pyrazolylpyrazolines of formula (I) according to claim 1 with one or more extenders and/or surfactants.

18. A pyrazoline of formula (II)

(II)

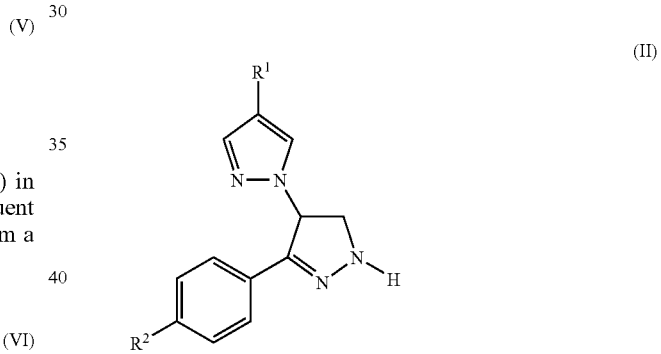

in which
R¹ represents optionally substituted hetaryl, and
R² represents halogen, haloalkyl, alkoxy, haloalkoxy, alkylthio, haloalkylthio, alkylsulphonyl, haloalkylsulphinyl, haloalkylsulphonyl, or cyano.

* * * * *